United States Patent
Gupta et al.

(10) Patent No.: US 11,339,381 B2
(45) Date of Patent: May 24, 2022

(54) NUCLEOTIDE SEQUENCE ENCODING 9-LIPOXYGENASE AND RECOMBINANT CONSTRUCTS COMPRISING THE SAME

(71) Applicant: Council of Scientific & Industrial Research, New Delhi (IN)

(72) Inventors: Vidya Shrikant Gupta, Pune (IN); Ashish Balwant Deshpande, Pune (IN); Hemangi Girish Chidley, Pune (IN); Ashok Prabhakar Giri, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 873 days.

(21) Appl. No.: 16/088,725

(22) PCT Filed: Mar. 31, 2017

(86) PCT No.: PCT/IN2017/050120
§ 371 (c)(1),
(2) Date: Sep. 26, 2018

(87) PCT Pub. No.: WO2017/168450
PCT Pub. Date: Oct. 5, 2017

(65) Prior Publication Data
US 2021/0324348 A1    Oct. 21, 2021

(30) Foreign Application Priority Data
Mar. 31, 2016  (IN) .............. 201611011374

(51) Int. Cl.
*C12N 9/02* (2006.01)
*C12N 1/20* (2006.01)
*C12N 15/70* (2006.01)
*C12R 1/19* (2006.01)
*C12N 15/74* (2006.01)

(52) U.S. Cl.
CPC ............ *C12N 9/0069* (2013.01); *C12N 1/20* (2013.01); *C12N 15/70* (2013.01); *C12N 15/743* (2013.01); *C12N 2523/00* (2013.01); *C12R 2001/19* (2021.05); *C12Y 113/11058* (2013.01)

(58) Field of Classification Search
CPC .................................................. C12N 9/0069
See application file for complete search history.

(56) References Cited

PUBLICATIONS

Idstein et al., "Volatile Constituents of Alphonso Mango (*Mangifera indica*)", Phytochemistry, vol. 24, No. 10, 1985, pp. 2313-2316.
Chidley et al., "Spatial and temporal changes in the volatile profile of Alphonso mango upon exogenous ethylene treatment", Food Chemistry vol. 136, 2013, pp. 585-594.
Huang et al., "Cloning and characterization of a 9-lipoxygenase gene induced by pathogen attack from Nicotiana benthamiana for biotechnological application", BMC Biotechnology, 2011 11:30, pp. 1-15.

(Continued)

*Primary Examiner* — Yong D Pak
(74) *Attorney, Agent, or Firm* — Dinsmore & Shohl, LLP

(57) ABSTRACT

The present invention provides a polynucleotide having the nucleotide sequence as set forth in SEQ ID NO: 1 encoding 9-lipoxygenase. The present invention also provides recombinant plasmid expression vector comprising said polynucleotide. The recombinant protein 9-lipoxygenase encoded by the polynucleotide leads to production of lactones in fruits such as mangoes.

12 Claims, 11 Drawing Sheets

Specification includes a Sequence Listing.

(56) References Cited

PUBLICATIONS

Santino et al., "Cloning and characterisation of an almond 9-lipoxygenase expressed early during seed development", Plant Science 168, 2005, pp. 699-706.

Padilla et al., "Mlelcular cloning, functional characterization and transcriptional regulation of a 9-lipoxygenase gene from olive", Phytochemistry, 74, 2012, pp. 58-68.

Kapila et al., "An Agrobacterium-mediated transient gene expression system for intact leaves", Plant Science, 122,1997, pp. 101-108.

Koncz et al., "The promoter of TL-DNA gene 5 controls the tissue-specific expression of chimaeric genes carried by a novel type of Agrobacterium binary vector", Molecular General Genetics, vol. 204, No. 3, 1986, pp. 383-396.

Spolaore et al., "A simple protocol for transient gene expression in ripe fleshy fruit mediated by Agrobacterium", Journal of Experimental Botany, vol. 52, No. 357, 2001, pp. 845-850.

International Search Report and Written Opinion pertaining to International Application No. PCT/IN2017/050120, filed Mar. 31, 2017, 10 pages.

XP-002771690,<BNSDOCID: XP_2771690A_1_>, 2 pages.

Pandit, et al., Expression profiling of various genes during the fruit development and ripening of mango, Plant Physiology and Biochemistry, vol. 48, 2010, pp. 426-433, India.

Wilson, et al., Importance of Some Lactones and 2,5-Dimethyl-4-hydroxy-3(2H)-furanone to Mango (*Mangifera indica* L.) Aroma, J. Agric. Food Chem., 1990, vol. 38, pp. 1556-1559, American Chemical Society, USA.

Zhang, et al., Volatiles Production and Lipoxygenase Gene Expression in Kiwifruit Peel and Flesh During Fruit Ripening, J. American Society Horticulture, Science, 2009, vol. 134, Issue 4, pp. 472-477, USA.

Deshpande, et al., Isolation and characterization of 9-lipoxygenase and epoxide hydrolase 2 genes: Insight into lactone biosynthesis in mango fruit (*Mangifera indica* L.), Phytochemistry, 2017, pp. 65-75, India.

SEQUENCE LISTING

<160> NUMBER OF SEQ ID NOS: 11

<210> SEQ ID NO 1
<211> LENGTH: 2526
<212> TYPE: DNA
<213> ORGANISM: Artificial Sequence
<220> FEATURE:
<223> OTHER INFORMATION: Recombinant DNA

<400> SEQUENCE: 1

```
atggggacag tggtgttgat gaagaagaat tttttggact tcaatgacct cagtgcatcg      60
gttattgatc gtgttgatga actggttggt aaaagagtct ctttgcagct cgttagtgct     120
tttaactctg accctactgc atcaaatggg ctgcaaggaa aggttggaga gccagcacat     180
ttggaagagt ggattactac aatcactcct ttggtagcag aggaatcgac attcaaggtc     240
acatttgatt gggatgaaca gattggagtt ccaggagcat tcataataaa gaacaatcat     300
cacagtggat tttacttgaa atctctcaca cttgaggatg ttcctaatca gggtcggatt     360
cactttgtat gcaactcctg ggtttatcct gcaaaacgct ataagaaaga tcgcgttttc     420
ttcaccaaca agacatacct tccaggtgaa atgccggcac cattacaata ttatagagag     480
caagaactcc taaacttgag aggagatgga actggagagc ttcaagaatg ggacagagtc     540
tatgactatg cgtactataa tgatttgggt gatccggaca atggcaaacc acgaccagtt     600
cttgagggt ctactgagta tccttatcct cgtaggggaa gaacaggcag accaccagca     660
aaaacagatc ctgagactga gagcaggctg ccacttctga cgagcttaaa catctatgtt     720
ccaagagatg agcgatttgg tcacataaaa atgtcagatt ttcttggtta tgcactgaaa     780
tccatatctc aattcattga ccagcgttg gaatctgtat ttgacagcac cccaaatgaa     840
tttgacaact tgctcaaat atacaaactc tacgatgaag ggattcagct tcctaatgac     900
cattttcttg atgatattag aataatatc cccttagaat tgctcaagga attttttcca     960
accaatgagg ataatctctt tgaattccca caccacagg tgatccaagg ggataggtct    1020
gcatggagaa ccgatgaaga gtttgcaaga gaaatgctgg ctggaccgaa ccctgtgatc    1080
attcgccgag ttgaggaatt ccctccaaga agcaagctcg accctgaact atatggtgat    1140
caagatagta agataaccaa acagcacata gagagctact tagatgggct gactgtagag    1200
caggcaattg agaagaacga gctattcata ttggatcacc atgattcact gatgacatac    1260
ttgagaagga taaacactac ttccacaaag acttatgcat ccaggacaat cctttttctta    1320
aaagaggatg gaactttgaa accactggca attgaattga gcaggccaca tcctgatgga    1380
gatcaatatg gtgccatcag caacgtttac acgccatcag aagatgaagt ggaaggttcc    1440
atatggcagc tggctaaagc ttatgtggct gtaaatgact ctggtgttca tcagctcatc    1500
agccactggt tgaagactca tgcagcaatt gagccatttg tgatagcaac aaatcggcaa    1560
ctgagtgtgc ttcacccaat ttataagctt ctgcaacctc atttccgtga cacaatgaat    1620
ataaatgcgt ttgctcgtca gatcgtcatt aatgcgggtg aattctgga actacggtt     1680
ttccctgcaa agtatgccat ggaaatgtca tctgcaatct acaaagactg gacttttcca    1740
gatcaggcac ttcctgaaga cctcaagaat agggaatgg cagttgagga ccccaactct    1800
ccacatggtc ttcgcctact gatagcagac tacccatatg ctgttgatgg gcttgaaatc    1860
tggtttgcaa taaaaactg ggtcaaagac tattgctact ctactacaa aagcgatgaa    1920
atgatgcaaa aggatagtgg actgcaatcc tggtggaagg aactacgcga ggagggtcat    1980
ggtgacaaga aagatgagcc ctggtggcct aaaatgcaaa atcgtgaaga gctgatagag    2040
gcatgcacca taatcatatg gatagcttcc gctctccatg ctgctgtcaa ttttggacag    2100
tatccttatg caggtttcct ccctaaccgt ccaactatga gtcgaagatt catgcctgaa    2160
aaaggaactc ctgattatga tgagctagag tcgaatttcg acaaagtgtt cctgaaaacg    2220
atcactgctc agcggcagac tcttcttggc attgctctta tagagacttt gtcaaggcat    2280
```

```
tcatcggatg agatgtacct gggacaaaga gacacacctg aatggacatc agataaaatt    2340
cccttgcaag catttgagga cttcggaaag aaattgggag acattgaagt aagaatcata    2400
acaagaaatc atgacaatat gctcaagaac cgcgttggcc ctgtcaatat gccatacact    2460
ttgctttatc ctaccagtga aggtggcctt actggcaaag gaattccaaa cagtgtttca    2520
atttag                                                               2526
```

<210> SEQ ID NO 2
<211> LENGTH: 841
<212> TYPE: PRT
<213> ORGANISM: Artificial Sequence
<220> FEATURE:
<223> OTHER INFORMATION: Protein sequence of 7- Dehydrocholestrol reductase (7-DHCR)

<400> SEQUENCE: 2

```
Met Gly Thr Val Val Leu Met Lys Lys Asn Phe Leu Asp Phe Asn Asp
1               5                   10                  15

Leu Ser Ala Ser Val Ile Asp Arg Val Asp Glu Leu Val Gly Lys Arg
            20                  25                  30

Val Ser Leu Gln Leu Val Ser Ala Phe Asn Ser Asp Pro Thr Ala Ser
        35                  40                  45

Asn Gly Leu Gln Gly Lys Val Gly Glu Pro Ala His Leu Glu Glu Trp
    50                  55                  60

Ile Thr Thr Ile Thr Pro Leu Val Ala Glu Glu Ser Thr Phe Lys Val
65                  70                  75                  80

Thr Phe Asp Trp Asp Glu Gln Ile Gly Val Pro Gly Ala Phe Ile Ile
                85                  90                  95

Lys Asn Asn His His Ser Gly Phe Tyr Leu Lys Ser Leu Thr Leu Glu
            100                 105                 110

Asp Val Pro Asn Gln Gly Arg Ile His Phe Val Cys Asn Ser Trp Val
        115                 120                 125

Tyr Pro Ala Lys Arg Tyr Lys Lys Asp Arg Val Phe Phe Thr Asn Lys
    130                 135                 140

Thr Tyr Leu Pro Gly Glu Met Pro Ala Pro Leu Gln Tyr Tyr Arg Glu
145                 150                 155                 160

Gln Glu Leu Leu Asn Leu Arg Gly Asp Gly Thr Gly Glu Leu Gln Glu
                165                 170                 175

Trp Asp Arg Val Tyr Asp Tyr Ala Tyr Tyr Asn Asp Leu Gly Asp Pro
            180                 185                 190

Asp Asn Gly Lys Pro Arg Pro Val Leu Gly Gly Ser Thr Glu Tyr Pro
        195                 200                 205

Tyr Pro Arg Arg Gly Arg Thr Gly Arg Pro Ala Lys Thr Asp Pro
    210                 215                 220

Glu Thr Glu Ser Arg Leu Pro Leu Leu Thr Ser Leu Asn Ile Tyr Val
225                 230                 235                 240

Pro Arg Asp Glu Arg Phe Gly His Ile Lys Met Ser Asp Phe Leu Gly
                245                 250                 255

Tyr Ala Leu Lys Ser Ile Ser Gln Phe Ile Glu Pro Ala Leu Glu Ser
            260                 265                 270

Val Phe Asp Ser Thr Pro Asn Glu Phe Asp Asn Phe Ala Gln Ile Tyr
        275                 280                 285

Lys Leu Tyr Asp Glu Gly Ile Gln Leu Pro Asn Asp His Phe Leu Asp
    290                 295                 300

Asp Ile Arg Asn Asn Ile Pro Leu Glu Leu Leu Lys Glu Ile Phe Pro
```

```
                305                 310                 315                 320
Thr Asn Glu Asp Asn Leu Phe Glu Phe Pro Thr Pro Gln Val Ile Gln
                    325                 330                 335
Gly Asp Arg Ser Ala Trp Arg Thr Asp Glu Glu Phe Ala Arg Glu Met
                    340                 345                 350
Leu Ala Gly Pro Asn Pro Val Ile Ile Arg Arg Val Glu Glu Phe Pro
                    355                 360                 365
Pro Arg Ser Lys Leu Asp Pro Glu Leu Tyr Gly Asp Gln Asp Ser Lys
                    370                 375                 380
Ile Thr Lys Gln His Ile Glu Ser Tyr Leu Asp Gly Leu Thr Val Glu
385                 390                 395                 400
Gln Ala Ile Glu Lys Asn Glu Leu Phe Ile Leu Asp His His Asp Ser
                    405                 410                 415
Leu Met Thr Tyr Leu Arg Arg Ile Asn Thr Thr Ser Thr Lys Thr Tyr
                    420                 425                 430
Ala Ser Arg Thr Ile Leu Phe Leu Lys Glu Asp Gly Thr Leu Lys Pro
                    435                 440                 445
Leu Ala Ile Glu Leu Ser Arg Pro His Pro Asp Gly Asp Gln Tyr Gly
                    450                 455                 460
Ala Ile Ser Asn Val Tyr Thr Pro Ser Glu Asp Val Glu Gly Ser
465                 470                 475                 480
Ile Trp Gln Leu Ala Lys Ala Tyr Val Ala Val Asn Asp Ser Gly Val
                    485                 490                 495
His Gln Leu Ile Ser His Trp Leu Lys Thr His Ala Ala Ile Glu Pro
                    500                 505                 510
Phe Val Ile Ala Thr Asn Arg Gln Leu Ser Val Leu His Pro Ile Tyr
                    515                 520                 525
Lys Leu Leu Gln Pro His Phe Arg Asp Thr Met Asn Ile Asn Ala Phe
                    530                 535                 540
Ala Arg Gln Ile Val Ile Asn Ala Gly Gly Ile Leu Glu Thr Thr Val
545                 550                 555                 560
Phe Pro Ala Lys Tyr Ala Met Glu Met Ser Ser Ala Ile Tyr Lys Asp
                    565                 570                 575
Trp Thr Phe Pro Asp Gln Ala Leu Pro Glu Asp Leu Lys Asn Arg Gly
                    580                 585                 590
Met Ala Val Glu Asp Pro Asn Ser Pro His Gly Leu Arg Leu Leu Ile
                    595                 600                 605
Ala Asp Tyr Pro Tyr Ala Val Asp Gly Leu Glu Ile Trp Phe Ala Ile
                    610                 615                 620
Lys Asn Trp Val Lys Asp Tyr Cys Tyr Phe Tyr Tyr Lys Ser Asp Glu
625                 630                 635                 640
Met Met Gln Lys Asp Ser Gly Leu Gln Ser Trp Lys Glu Leu Arg
                    645                 650                 655
Glu Glu Gly His Gly Asp Lys Asp Glu Pro Trp Trp Pro Lys Met
                    660                 665                 670
Gln Asn Arg Glu Glu Leu Ile Glu Ala Cys Thr Ile Ile Trp Ile
                    675                 680                 685
Ala Ser Ala Leu His Ala Ala Val Asn Phe Gly Gln Tyr Pro Tyr Ala
                    690                 695                 700
Gly Phe Leu Pro Asn Arg Pro Thr Met Ser Arg Arg Phe Met Pro Glu
705                 710                 715                 720
Lys Gly Thr Pro Asp Tyr Asp Glu Leu Glu Ser Asn Phe Asp Lys Val
                    725                 730                 735
```

```
Phe Leu Lys Thr Ile Thr Ala Gln Arg Gln Thr Leu Leu Gly Ile Ala
            740                 745                 750
Leu Ile Glu Thr Leu Ser Arg His Ser Ser Asp Glu Met Tyr Leu Gly
        755                 760                 765
Gln Arg Asp Thr Pro Glu Trp Thr Ser Asp Lys Ile Pro Leu Gln Ala
770                 775                 780
Phe Glu Asp Phe Gly Lys Lys Leu Gly Asp Ile Glu Val Arg Ile Ile
785                 790                 795                 800
Thr Arg Asn His Asp Asn Met Leu Lys Asn Arg Val Gly Pro Val Asn
            805                 810                 815
Met Pro Tyr Thr Leu Leu Tyr Pro Thr Ser Glu Gly Gly Leu Thr Gly
        820                 825                 830
Lys Gly Ile Pro Asn Ser Val Ser Ile
        835                 840

<210> SEQ ID NO 3
<211> LENGTH: 4499
<212> TYPE: DNA
<213> ORGANISM: Mangifera indica

<400> SEQUENCE: 3
atggggacag tggtgttgat gaagaagaat tttttggact tcaatgacct cagtgcatcg     60
gttattgatc gtgttgatga actggttggt aaaagagtct ctttgcagct cgttagtgct    120
tttaactctg accctactgc atgtgagttc ttcttctttt ctctttactt gcaccttttt    180
cttttttaga tctctggttt cttctgctct ttttcttggg tttgatgctg ctgtttgtgg    240
ccacaaaaaa agaaagcctg cagcttcctc accatgcaat aactattcat gtgtgaaaag    300
ggaaaaatgt gcagaaactt gaagaacaaa cttcttttct atttgtcttt ggtttgaaaa    360
tattacaagt agtaagttag tttgatgtgg gcatttaaaa ctcacctttt cagttagttt    420
ttgggattga gagagactcg atattacttt tcgaggcctt aacacagtcc ttgtggttcg    480
aggtcgaact atagtaaaat cccaaaccag ggacggtcgt ttcttatgat atccaacgtt    540
ttctctatga atttatagca tatctctata tttgactttg gggaagtttt gtgttatctc    600
tatatatatg atgaggaata agagtttggc ctatagtttt tactgtcttc tgtcctcttt    660
tgggtaaaaa ggacagatga gtcatgataa aaatggctat gtaaattgaa caccgtaata    720
tgttcacaga gatatagtta tggcagttca taaatatgag ctttaacaag ttttttccat    780
taatgaattg tgttaccaaa agaagattcg gcagaagcag ggcagggtct gaactgtttc    840
actaattgct tgtttgtttt taggtgacaa ttgaaagttg gaggtctccc aagtctcaaa    900
cagaaaaaag ttatcattta atcggccttt tcttttgttt cttatttta a agtcgactag    960 aatattacca agtctttgtt ttttacttg taatctaact tgacaaatgg ggcatgacct    1020
atttgacatt ttcttatgtt ttcaaaacac aattcatcaa aactaacaaa tgttataatt    1080
taatataatt tcaaggttaa accatatatt aggtaaaact ccctatctta aaaacctaaa    1140
tgccaaatct gaacaggatg atgattaaaa tcctttttaa ttattaaatc atattgactt    1200
aaaattaaat tgattggata gtattaaatc ataattcaat tgttgagtta gattgatctg    1260
atcgttacaa tgatgtcatt cggatgctac ataattaaaa tttattttaa aactttgttg    1320
attgatcctt tgaccaagtc aacgttgatc caatttaaaa acatggggta aattatatta    1380
attttcctga taattaaacc tgggtcaata attttggcag ttcattgatt gttaagaagt    1440
tgtaatgaag tgatgtaatt catttcatca aagccttaat agttagagaa taaaaaatag    1500
```

```
gaacttgaag agggaatgaa gaattttttta ccttttcaat gaatatgcca ttaatttatt    1560
tttgaactat cacctaattt gaaaatgaaa ttaatgagtg tgtcaatgaa tatttgatgt    1620
gtgtgtgtgg atgcagcaaa tgggctgcaa ggaaaggttg gagagccagc acatttggaa    1680
gagtggatta ctacaatcac tcctttggta gcagaggaat cgacattcaa ggtcacattt    1740
gattgggatg aacagattgg agttccagga gcattcataa taaagaacaa tcatcacagt    1800
ggattttact tgaaatctct cacacttgag gatgttccta atcagggtcg gattcacttt    1860
gtatgcaact cctgggttta tcctgcaaaa cgctataaga aagatcgcgt tttcttcacc    1920
aacaaggcaa gtatagtttt gatacaatta atttcctaca agtgattatg agtcttgtac    1980
taagtttatg tcaactattt ttctgcagac ataccttcca ggtgaaatgc cggcaccatt    2040
acaatattat agagagcaag aactcctaaa cttgagagga gatggaactg gagagcttca    2100
agaatgggac agagtctatg actatgcgta ctataatgat ttgggtgatc cggacaatgg    2160
caaaccacga ccagttcttg agggtctact gagtatcct tatcctcgta ggggaagaac     2220
aggcagacca ccagcaaaaa caggtaccgt tccattggta tgtttggaga atattaagt    2280
cttatcagtg caattggcat tgtcattgac agtttggtta ttgttgtaac agatcctgag    2340
actgagagca ggctgccact tctgacgagc ttaaacatct atgtcccaag agatgagcga    2400
tttggtcaca taaaaatgtc agattttctt ggttatgcac tgaaatccat atctcaattc    2460
attgagccag cgttggaatc tgtatttgac agcaccccaa atgaatttga caactttgct    2520
caaatataca aactctacga tgaagggatt cagcttccta atgaccattt tcttgatgat    2580
attagaaata atatcccctt agaattgctc aaggagattt ttccaaccaa tgaggataat    2640
ctctttgaat tcccaacacc acaggtgatc caaggtaatg tgagacattt ctagccgatc    2700
ctctatttgc catataacag atttaagttt gtgcttctat acatttttca ttttcctgtt    2760
tttaatgttt taataccttg gagcagggga taggtctgca tggagaaccg atgaagagtt    2820
tgcaagagaa atgctggctg gaccgaaccc tgtcatcatt cgccgagttg aggtaaagat    2880
tttgtaacaa gttttctttc tctcattttc ttcttcacca agaaagtaga tgccttgtga    2940
tattttctga taaaaattac taaaataatt gcagcaattc cctccaagaa gcaagctcga    3000
ccctgaacta tatggtgatc aagatagtaa gataaccaaa cagcacatag agagctactt    3060
agatgggctg actgtagagc aggtaccccca acagtcttgt gatcctttg tgattgtaat    3120
ttcttaatat gagtctttaa ccaaacaaat taacaagtga tttcgatttg gtataggcaa    3180
ttgagaagaa caagctattc atattggatc accatgattc actgatgaca tacttgagaa    3240
ggataaacac tacttccaca aagacttatg catccaggac aatccttttc ttaaaagagg    3300
atggaacttt gaaaccactg gcaattgaat tgagcaggcc acatcctgat ggagatcaat    3360
atggtgccat cagcaacgtt tacacgccat cagaagatga agtggaaggt tccatatggc    3420
agctggctaa agcttatgtg gctgtaaatg actctggtgt tcatcagctc atcagccact    3480
ggttgaagac tcatgcagca attgagccat tgtgatagc aacaaatcgg caactgagtg     3540
tgcttcaccc aatttataag cttctgcaac ctcatttccg tgacacaatg aatataaatg    3600
cgtttgctcg tcagatcgtc attaatgcgg gtggaattct ggaaactacg gttttccctg    3660
caaagtatgc catggaaatg tcatctgcaa tctacaaaga ctggactttt ccagatcagg    3720
cacttcctga agacctcaag aatagaggaa tggcagttga ggaccccaac tctccacatg    3780
gtcttcgcct actgatagca gactacccat atgctgttga tgggcttgaa atctggtttg    3840
```

-continued

```
caataaaaaa ctgggtcaaa gactattgct acttctacta caaaagcgat gaaatgatgc    3900
aaaaggatag tggactgcaa tcctggtgga aggaactacg cgaggagggt catggtgaca    3960
agaaagatga gccctggtgg cctaaaatgc aaaatcgtga agagctgata gaggcatgca    4020
ccataatcat atggatagct tccgctctcc atgctgctgt caattttgga cagtatcctt    4080
atgcaggttt cctccctaac cgtccaacta tgagtcgaag attcatgcct gaaaaggaa     4140 ctcctgatta tgatgagcta gagtcgaatt tcgacaaagt gttcctgaaa acgatcactg    4200
ctcagcggca gactcttctt ggcattgctc ttatagagac tttgtcaagg cattcatcgg    4260
atgagatgta cctgggacaa agagacacac ctgaatggac atcagataaa atccccttgc    4320
aagcattcga ggacttcgga aagaaattgg gagacattga agtaagaatc ataacaagaa    4380
atcatgacaa tatgctcaag aaccgcgttg gccctgtcaa tgtgccatac actttgcttt    4440
atcctaccag tgaaggtggc cttactggca aggaattcc aaacagtgtt tcaatttag     4499
```

<210> SEQ ID NO 4
<211> LENGTH: 22
<212> TYPE: DNA
<213> ORGANISM: Artificial Sequence
<220> FEATURE:
<223> OTHER INFORMATION: LF1_primer

<400> SEQUENCE: 4
gggatccgga caatggcaaa cc         22

<210> SEQ ID NO 5
<211> LENGTH: 19
<212> TYPE: DNA
<213> ORGANISM: Artificial Sequence
<220> FEATURE:
<223> OTHER INFORMATION: LR3_primer

<400> SEQUENCE: 5
cctccaagaa ctggtcgtg             19

<210> SEQ ID NO 6
<211> LENGTH: 24
<212> TYPE: DNA
<213> ORGANISM: Artificial Sequence
<220> FEATURE:
<223> OTHER INFORMATION: LOX_TF1_primer

<400> SEQUENCE: 6
atggggacag tggtgttgat gaag       24

<210> SEQ ID NO 7
<211> LENGTH: 27
<212> TYPE: DNA
<213> ORGANISM: Artificial Sequence
<220> FEATURE:
<223> OTHER INFORMATION: LOX_TR1_primer

<400> SEQUENCE: 7
ctaaattgaa acactgtttg gaattcc     27

<210> SEQ ID NO 8
<211> LENGTH: 28
<212> TYPE: DNA
<213> ORGANISM: Artificial Sequence
<220> FEATURE:
<223> OTHER INFORMATION: LOX_ pET101D F1

<400> SEQUENCE: 8

```
caccatgggg acagtggtgt tgatgaag                                              28

<210> SEQ ID NO 9
<211> LENGTH: 28
<212> TYPE: DNA
<213> ORGANISM: Artificial Sequence
<220> FEATURE:
<223> OTHER INFORMATION: LOX_ pET101D R1

<400> SEQUENCE: 9
aattgaaaca ctgtttggaa ttcctttg                                              28

<210> SEQ ID NO 10
<211> LENGTH: 36
<212> TYPE: DNA
<213> ORGANISM: Artificial Sequence
<220> FEATURE:
<223> OTHER INFORMATION: LOXpBI121_F1

<400> SEQUENCE: 10
aaaaaaggat ccatggggac agtggtgttg atgaag                                     36

<210> SEQ ID NO 11
<211> LENGTH: 39
<212> TYPE: DNA
<213> ORGANISM: Artificial Sequence
<220> FEATURE:
<223> OTHER INFORMATION: LOXpBI121_R1

<400> SEQUENCE: 11
aaaaaaggat ccctaaattg aaacactgtt tggaattcc                                  39
```

NUCLEOTIDE SEQUENCE ENCODING 9-LIPOXYGENASE AND RECOMBINANT CONSTRUCTS COMPRISING THE SAME

FIELD OF THE INVENTION

The present invention relates to a polynucleotide encoding recombinant 9-lipoxygenase for lactone synthesis. The recombinant 9-lipoxygenase is expressed in an expression vector.

BACKGROUND AND PRIOR ART OF THE INVENTION

India being the largest producer of mango globally contributes to nearly 40% of the total world production. India scores over other countries when it comes to mango production, due to favoured availability of natural resources and climatic conditions. The unique aroma and flavour of mangoes is rendered by presence of various aromatic volatile organic chemicals mainly belonging to terpene, furanone, lactone and ester classes which are synthesized and released during developmental and ripening stages of different mango cultivars. Despite being bestowed with favourable cultivation conditions, Indian cultivators are encountering grave challenges leading to a negative mango growth rate. Further, cultivation of Alphonso mangoes is troublesome to farmers because of various factors such as cultivation locality dependent variation in the fruit quality, especially in terms of flavour; occurrence of physiological diseases such as malformation of mangoes, abnormal ripening, bacterial parasitic and fungal diseases; and alternate bearing of the fruits.

Alphonso' cultivar has been found to have qualitative and quantitative dominance of lactones. These oxygenated volatile compounds are known for their creamy, caramel, coconut, fruity or peach like aromatic notes based on the type of lactones and low detection threshold thereby significantly contributing to the aroma of the mango cultivars. Moreover, Idstein and Schreier (1985) showed that the aroma of 'Alphonso' is contributed by 14 different γ and δ-lactones. No other mango cultivar or other fruit is known to possess such diversity of lactones. Lactones have a low odor detection threshold thus contributing more odor units to the fruit though present in minor quantities. Therefore, a standard pathway leading to the synthesis of lactones will help address the problem of lactone synthesis in mangoes. However, there has been no prior teaching indicating the pathway for the synthesis of lactones in mangoes.

A few studies have suggested that the biosynthesis of lactones may be from unsaturated, epoxy and hydroxy fatty acids. The probable pathway of lactone biosynthesis in mango is from hydroxy fatty acids, which are formed by fatty acid oxidation by mono-oxygenase and di-oxygenase enzymes and their downstream processing. Lipoxygenase is an important di-oxygenase and has various isoforms viz. 9-lipoxygenase, 13-lipoxygenase, and 5-lipoxygenase. However, the gene and the corresponding lipoxygenase protein from mango have not been studied for its probable involvement in lactone biosynthesis.

A research study providing the expression profiling of various genes during the fruit development and ripening of mango by Pandit et al (Journal Plant Physiol. Biochem. 48 (6), 426-433 (2010)) discloses that the development and ripening stages in mango are programmed processes and conventional indices and volatile markers help to determine agronomically important stages of fruit life. With reference to lipoxygenase, it was noted that the ripening induced expression of the LOX gene in mango. However, no reference is made to the role of lipoxygenase in the synthesis of lactones. Further, the mRNA sequence disclosed in the corresponding citation EU513272.1 of the Genbank repository is only the partial sequence and does not encode the complete and functional 9-lipoxygenase enzyme.

In another research article, by Bo Zhang et al, (AMER. SOC. HORT. SCI. 134(4):472-477. 2009. titled, 'Volatiles Production and Lipoxygenase Gene Expression in Kiwifruit Peel and Flesh During Fruit Ripening') the relationship between lipoxygenase (LOX) pathway-derived volatiles and LOX gene expression in kiwifruit (*Actinidia deliciosa*) during postharvest ripening at 20° C. is evaluated. The possible roles of LOX genes in relation to kiwi fruit volatile formation during fruit ripening is disclosed, however, the authors fail to indicate the specific volatiles that may be the result of the action of lipoxygenase.

As observed from the above disclosures, there have been no attempts in the art to disclose important enzymes in the synthesis of lactones, which impart creamy, caramel, coconut, fruity or peach like aromatic notes based on the type of lactones in mangoes.

Therefore, there is a need in the art to explore enzymes conferring flavor and aroma in mangoes to provide a sustained quality of mangoes.

OBJECTIVE OF THE INVENTION

An objective of the present invention is to provide a polynucleotide encoding recombinant 9-lipoxygenase.

Another objective of the present invention is to provide a process for synthesis of recombinant 9-lipoxygenase.

Yet another object of the present invention is to provide a composition comprising a host cell comprising the recombinant expression vector having the polynucleotide encoding recombinant 9-lipoxygenase and a culture medium.

Still another object of the present invention is to provide a method of enhancing the synthesis of lactone in fruit of a plant.

SUMMARY OF THE INVENTION

An aspect of the present invention provides a polynucleotide having the nucleotide sequence as set forth in SEQ ID NO: 1 encoding a recombinant protein 9-lipoxygenase.

Another aspect of the present invention provides a recombinant protein 9-lipoxygenase having amino acid sequence as set forth in SEQ ID NO: 2, which is encoded by the nucleotide sequence as set forth in SEQ ID NO: 1.

In another aspect of the present invention, the polynucleotide having the nucleotide sequence as set forth in SEQ ID NO: 1 is a cDNA.

Still another aspect of the present invention provides a recombinant plasmid expression vector comprising polynucleotide having the nucleotide sequence as set forth in SEQ ID NO: 1, wherein the plasmid expression vector is selected from the group consisting of pGEMT, pET101D, and pBI121.

Yet another aspect of the present invention provides an in-vivo transient over expression of 9-lipoxygenase in ripening mango fruits.

Another aspect of the present invention provides a process for synthesis of recombinant 9-lipoxygenase comprising:

a) synthesizing polynucleotide having the nucleotide sequence as set forth in SEQ ID NO: 1 with primers selected from the group consisting of SEQ ID NO: 4, SEQ ID NO:5, SEQ ID NO: 6, and SEQ ID NO: 7;

b) cloning the polynucleotide having the nucleotide sequence as set forth in SEQ ID NO: 1 obtained in step (a) into a plasmid expression using the expression vector specific primers to obtain a recombinant plasmid expression vector;

c) transforming the recombinant plasmid expression vector obtained in step (b) into a host cell to obtain a transformed host cell;

d) culturing the transformed host cell obtained in step (c) at a temperature between 12° C. to 25° C. in a culture medium;

e) separating the recombinant host cells from the culture medium; and f) performing lysis and sonication of recombinant host cells to isolate the recombinant 9-lipoxygenase.

Yet another aspect of the present invention provides a composition comprising a host cell and a culture medium, wherein said host cell is having the recombinant plasmid expression vector comprising polynucleotide having the nucleotide sequence as set forth in SEQ ID NO: 1.

Still another aspect of the present invention provides a method of increasing the lactone content in fruits, comprising transforming a recombinant plasmid expression vector comprising the polynucleotide having the nucleotide sequence as set forth in SEQ ID NO: 1 in a host cell selected from a bacteria or a plant.

Yet another aspect of the present invention provides method of enhancing the synthesis of lactone in fruit of a plant comprising introducing the composition a composition comprising a host cell and a culture medium in fruit of a plant by agroinfiltration.

BRIEF DESCRIPTION OF THE DRAWINGS

FIG. 6(*b*) depicts a histogram representing changes in 9HpOTre (9-Hydroperoxy Octadeca Trienoic Acid) content with respect to control upon transient over expression of Mi9LOX. Vertical bars represent standard error in the values of lactones from used data set; significance is represented as ★p≤0.1; ★★p≤0.05.

FIG. 7(*b*) depicts transcript profiles of Mi9LOX from pulp tissue of various fruit development and ripening stages of Pairi mango cultivars. Vertical bars at each data point represent standard error in the relative quantification among the biological replicates. X axis represents fruit development and ripening stages and Y axis represents relative transcript abundance.

FIG. 7(*c*) depicts transcript profiles of Mi9LOX from pulp tissue of various fruit development and ripening stages of Kent mango cultivars. Vertical bars at each data point represent standard error in the relative quantification among the biological replicates. X axis represents fruit development and ripening stages and Y axis represents relative transcript abundance.

FIG. 8(*b*) depicts the transcript profiles of Mi9LOX from skin tissue of various fruit development and ripening stages of Pairi mango cultivars. Vertical bars at each data point represent standard error in the relative quantification among the biological replicates. X axis represents fruit development and ripening stages and Y axis represents relative transcript abundance.

FIG. 8(*c*) depicts the transcript profiles of Mi9LOX from skin tissue of various fruit development and ripening stages of Kent mango cultivars. Vertical bars at each data point represent standard error in the relative quantification among the biological replicates. X axis represents fruit development and ripening stages and Y axis represents relative transcript abundance.

FIG. 9(*b*) depicts the extracted ion chromatograms from High Resolution Mass Spectrometry (HRMS) analysis for product formed in assay reactions of Mi9LOX with substrate linoleic acid. X-axis represents retention time (min) and Y-axis represents relative intensity.

FIG. 9(*c*) depicts the extracted ion chromatograms from High Resolution Mass Spectrometry (HRMS) analysis for product identification of Mi9LOX assay reactions, for the protein expressed from empty vector with substrates linoleic acid. X-axis represents retention time (min) and Y-axis represents relative intensity.

FIG. 9(*d*) depicts the extracted ion chromatograms from High Resolution Mass Spectrometry (HRMS) analysis for product identification of Mi9LOX assay reactions, HpOTrE standard. X-axis represents retention time (min) and Y-axis represents relative intensity.

BRIEF DESCRIPTION OF SEQUENCE LISTING

Figure 1:
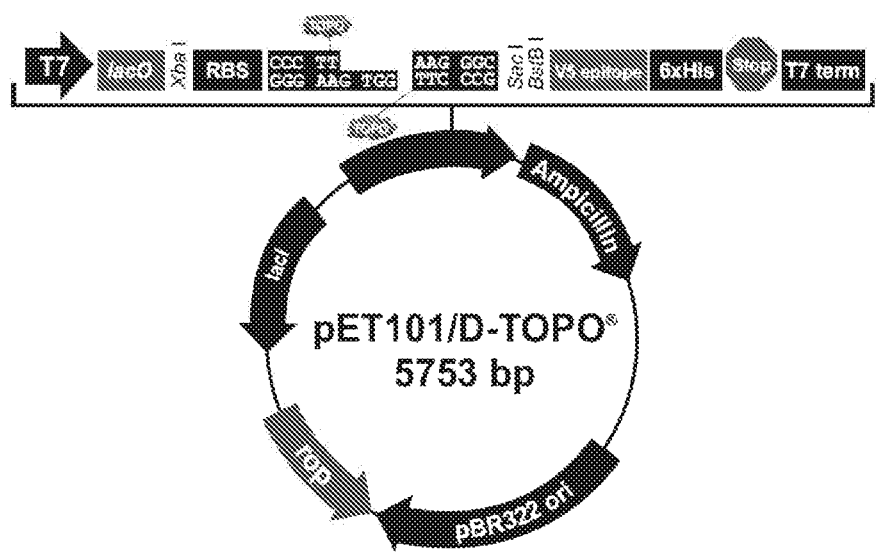
FIG. 1 depicts the pET101D/TOPO vector used to insert a 2526 base pair polynucleotide having the nucleotide sequence as set forth in SEQ ID NO: 1.

SEQ ID NO: 1 shows polynucleotide encoding recombinant 9-lipoxygenase (2526 bp)
SEQ ID NO: 2 shows amino acid sequence of 9-lipoxygenase (841 aa)
SEQ ID NO: 3 shows genomic sequence of 9-lipoxygenase from *Mangifera indica* (4499 bp)
SEQ ID NO: 4 shows forward primer LF1 (RACE primer) (22 bp)
SEQ ID NO: 5 shows reverse primer LR3 (RACE primer) (19 bp)
SEQ ID NO: 6 shows forward primer LOX_TF1 (24 bp)
SEQ ID NO: 7 shows reverse primer LOX_TR1 (27 bp)
SEQ ID NO: 8 shows forward primer LOX_pET101D F1 (28 bp)
SEQ ID NO: 9 shows reverse primer LOX_pET101D R1 (28 bp)
SEQ ID NO: 10 shows forward primer LOXpBI121_F1 (36 bp)
SEQ ID NO: 11 shows reverse primer LOXpBI121_R1 (36 bp)

DETAILED DESCRIPTION OF THE INVENTION

The invention will now be described in detail in connection with certain preferred and optional embodiments, so that various aspects thereof may be more fully understood and appreciated.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only". Similarly, "comprise", "comprises", "comprising", "include", "includes", and "including" are interchangeable and not intended to be limiting.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The term "transformation" means the transfer of nucleic acid (i.e., a nucleotide polymer) into a cell. As used herein, the term "genetic transformation" means the transfer and incorporation of DNA, especially recombinant DNA, into a cell.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Vector" is defined to include, inter alia, any plasmid, cosmid, phage or *Agrobacterium* binary vector in double or single stranded linear or circular form which may or may not be self-transmissible or mobilizable, and which can transform prokaryotic or eukaryotic host either by integration into the cellular genome or exist extrachromosomally (e.g. autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance. Various cloning vectors are available in the prior art.

Source of Biological Material:

The varieties of cv. Alphonso and cv. Pairi used in the present invention were collected from the Mango Research Sub Centre of Dr. Balasaheb Sawant Konkan Agricultural University, Dapoli situated at Deogad, Maharashtra, India (16° 31' N, 73° 20' E). Fruits of cv. Kent were collected from the Regional Fruit Research Station, Dr. Balasaheb Sawant Konkan Agricultural University, Vengurle, Maharashtra, India (15° 51' N, 73° 39' E).

Plasmid vectors were commercially obtained/purchased, cloning vector-pGEMT was obtained from Promega, Wis., USA; bacterial expression vector-pET101D was procured from Invitrogen, Carlsbad, Calif., USA and plant expression vector-pBI121 was obtained from Clontech, Palo, Alto, Calif. NCBI Accession No. AF485783.

*E. coli* BL21 was purchased from Novagen, Madison, Wis., USA.

*Agrobacterium* strain GV3101 is employed as referred to by Koncz and Schell, 1986.

An embodiment of the present invention provides a polynucleotide having the nucleotide sequence as set forth in SEQ ID NO: 1 encoding a recombinant protein 9-lipoxygenase In another embodiment of the present invention, there is provided a recombinant protein 9-lipoxygenase having amino acid sequence as set forth in SEQ ID NO: 2 encoded by the polynucleotide having the nucleotide sequence as set forth in SEQ ID NO: 1.

In yet another embodiment of the present invention there is provided a polynucleotide encoding a recombinant protein 9-lipoxygenase, wherein the polynucleotide is a cDNA.

Another embodiment of the present invention provides a plasmid expression vector comprising the polynucleotide having the nucleotide sequence as set forth in SEQ ID NO: 1.

In yet another embodiment of the present invention there is provided a plasmid expression vector comprising the polynucleotide having the nucleotide sequence as set forth in SEQ ID NO: 1, wherein the plasmid expression vector is selected from the group consisting of a plant plasmid expression vector and a bacterial plasmid expression vector.

In still another embodiment of the present invention, there is provided a plasmid expression vector comprising the polynucleotide having the nucleotide sequence as set forth in SEQ ID NO: 1, wherein the plasmid expression vector is selected from the group consisting of pBI121, pET101D, and pGEMT.

Another embodiment of the present invention provides a host cell comprising the plasmid expression vector comprising the polynucleotide having the nucleotide sequence as set forth in SEQ ID NO: 1.

In yet another embodiment of the present invention there is provided a host cell comprising the plasmid expression vector, wherein the host cell is selected from the group consisting of *E. coli* BL21, *E. coli* Rosetta, and *Agrobacterium* (GV3101).

Accordingly, the polynucleotide having nucleotide sequence as set forth in SEQ ID NO: 1 encoding recombinant 9-lipoxygenase is a full length sequence having 2526 base pairs. The recombinant 9-lipoxygenase has a length of 841 aa having sequence set forth in SEQ ID NO: 2. The polynucleotide having nucleotide sequence as set forth in SEQ ID NO: 1 is inserted in a plasmid vector, preferably pET101D (FIG. 1), to obtain a recombinant vector construct which is expressed in host cells selected from *E. coli* BL21 or *E. coli* Rosetta.

The genomic sequence of 9-lipoxygenase from *Mangifera indica* was isolated by the inventors of the present application. The sequence is as set forth in SEQ ID NO: 3. However, the cDNA sequence as set forth in SEQ ID NO: 1 encoding functional 9-lipoxygenase which plays a role in the synthesis of lactones thereby imparting a peculiar flavour characteristic to Alphonso mangoes is disclosed in the present application.

Lipoxygenase is an upstream enzyme, which acts on unsaturated fatty acids in di-oxygenase pathway. This enzyme utilizes unsaturated fatty acids as a substrate and oxygen as co-substrate and catalyzes the reaction to form hydroperoxy fatty acid. These hydroperoxy fatty acids are further diverted to many pathways like HPL pathway synthesizing C6 Green Leafy Volatiles, Oxylipin pathway producing Jasmonic acid. These hydroxy fatty acids are involved in lactone biosynthesis. Therefore, synthesis of polynucleotide encoding 9-lipoxygenase, an upstream enzyme in lactone production has resulted in a convenient method for the synthesis of volatile lactones.

In another embodiment of the present invention, there is provided primers for amplifying polynucleotide having nucleotide sequence as set forth in SEQ ID NO: 1, wherein the primers are selected from the group consisting of SEQ ID NO: 4, SEQ ID NO: 5, SEQ ID NO: 6 and SEQ ID NO: 7.

Gene specific primers SEQ ID NO: 4 and SEQ ID NO: 5 were designed from available partial sequence of 9-lipoxygenase from Alphonso mango to carry out 5' and 3' RACE reactions to obtain ends of cDNA.

```
SEQ ID NO. 4: Forward Primer: LF1:
GGGATCCGGACAATGGCAAACC

SEQ ID NO. 5: Reverse Primer LR3:
CCTCCAAGAACTGGTCGTG
```

Terminal primers for full length gene isolation were as follows:

```
SEQ ID NO. 6: Forward Primer LOX_TF1-:
ATGGGGACAGTGGTGTTGATGAAG

SEQ ID NO. 7: Reverse Primer LOX_TR1-:
CTAAATTGAAACACTGTTTGGAATTCC
```

Another embodiment of the present invention provides a process for synthesis of recombinant 9-lipoxygenase comprising:
a) synthesizing polynucleotide having the nucleotide sequence as set forth in SEQ ID NO: 1 with primers selected from the group consisting of SEQ ID NO: 4, SEQ ID NO:5, SEQ ID NO: 6, and SEQ ID NO: 7;
b) cloning the polynucleotide having the nucleotide sequence as set forth in SEQ ID NO: 1 obtained in step (a) into a plasmid expression vector using the expression vector specific primers to obtain a recombinant plasmid expression vector;
c) transforming the recombinant plasmid expression vector obtained in step (b) into a host cell to obtain a transformed host cell;
d) culturing the transformed host cell obtained in step (c) at a temperature ranging from 12° C. to 25° C. in a culture medium;
e) separating the recombinant host cells from the culture medium; and
f) performing lysis and sonication of recombinant host cells to isolate the recombinant 9-lipoxygenase.

In yet another embodiment of the present invention, there is provided a process for synthesis of recombinant 9-lipoxygenase, wherein the plasmid expression vector is selected from the group consisting of a plant expression vector pBI121 and a bacterial expression vector pET101D.

In still another embodiment of the present invention, there is provided a process for synthesis of recombinant 9-lipoxygenase, wherein the primers specific to pBI121 is selected from SEQ ID NO: 10 and SEQ ID NO: 11.

In another embodiment of the present invention, there is provided a process for synthesis of recombinant 9-lipoxygenase, wherein the primers specific to pET101D is selected from SEQ ID NO: 8 and 9.

In yet another embodiment of the present invention there is provided a process for synthesis of recombinant 9-lipoxygenase, wherein the host cell is selected from the group consisting of *E. coli* BL21, *E. coli* Rosetta, and *Agrobacterium* (GV3101).

In still another embodiment of the present invention, there is provided a process for synthesis of recombinant 9-lipoxygenase, wherein the culture medium is selected from the group consisting of YEB medium, yeast mannitol medium, YDPC medium and YEP medium.

The primers specific to pBI121 is selected from SEQ ID NO: 10 and SEQ ID NO: 11. The primer specific to pET101D is selected from SEQ ID NO: 8 and SEQ ID NO: 9.

Figure 3:
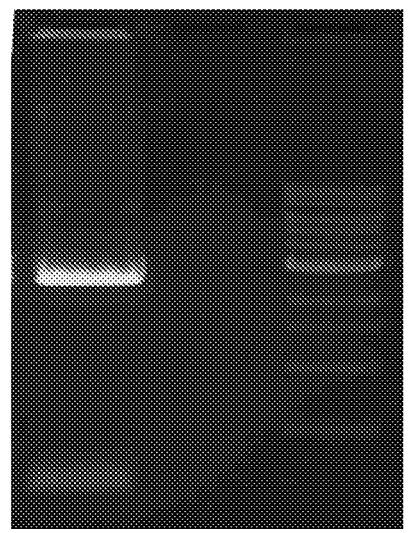
FIG. 3 depicts an approximately 2.5 kb size amplicon band on agarose gel, which is cloned in pET101D/TOPO vector, transformed in *E. coli* (Rosetta) competent cells.

Accordingly, an amplified polynucleotide sequence of 2.5 kb size band indicating polynucleotide having sequence set forth in SEQ ID NO: 1 was obtained on agarose gel as described in FIG. 3. This polynucleotide sequence was cloned in pGEM-T Easy vector, transformed in *E. coli* Top10 competent cells, thus indicating 9-lipoxygenase nucleotide sequence cloned in a cloning vector.

In another embodiment of the present invention, there is provided a plasmid vectors selected from cloning vector such as pGEMT plasmid vector, bacterial expression vector such as pET101D and plant expression vector such as pBI121.

Accordingly, the polynucleotide having nucleotide sequence as set forth in SEQ ID NO: 1 is cloned in bacterial expression vector pET101D using primers having SEQ ID NO: 8 and SEQ ID NO: 9 and transformed into *E. coli* BL21/Rosetta after confirming the correct orientation of the insert in the expression vector Further, the polynucleotide having nucleotide sequence as set forth in SEQ ID NO: 1 is cloned in a plant expression vector pBI121 using primers having SEQ ID NO: 10 and SEQ ID NO: 11 and transformed into *Agrobacterium* (GV3101).

An embodiment of the present invention provides composition comprising a host cell and a culture medium, wherein said host cell is having the recombinant plasmid expression vector comprising polynucleotide having the nucleotide sequence as set forth in SEQ ID NO: 1.

In another embodiment of the present invention, there is provided a composition comprising a host cell and a culture medium, wherein the culture medium is selected from the group consisting of YEB medium, yeast mannitol medium, YDPC medium and YEP medium.

Another embodiment of the present invention provides a method of enhancing the synthesis of lactone in fruit of a plant comprising introducing the composition comprising a host cell and a culture medium in fruit of a plant by agroinfiltration.

In another embodiment of the present invention, there is provided a method of enhancing the synthesis of lactone in fruit of a plant, wherein the plant is mango.

In another embodiment of the present invention, there is provided a method of enhancing the synthesis of lactone in fruit of a plant, wherein the lactone is selected from the group consisting of δ-valerolactone and δ-decalactone.

Accordingly, when the recombinant expression vector is inserted in a host cell, the lactone production increases.

Accordingly, the polynucleotide having the nucleotide sequence as set forth in SEQ ID NO: 1 is inserted in a plasmid vector, preferably pET101D, to obtain a recombinant vector construct, which may be inserted/transformed in a host cell such as bacterial expression system.

Accordingly, the poly nucleotide having the nucleotide sequence as set forth in SEQ ID NO: 1 is inserted in a plasmid vector, preferably pBI121, to obtain a recombinant vector construct, which when inserted/transformed in a host cell such as fruit/plant cells to carry out in vivo overexpression studies.

Figure 2:
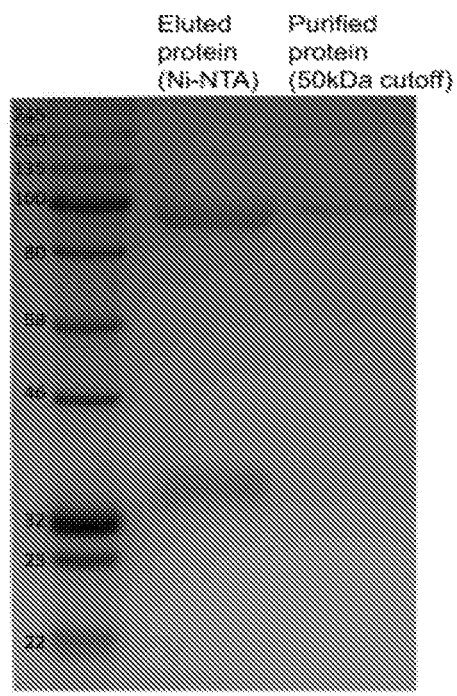
FIG. 2 depicts CBB stained SDS-PAGE gel representing purified recombinant Mi9LOX protein band near 100 kDa band of marker by Ni-NTA affinity purification, further purification of Mi9LOX by 50 kDa cut-off column to remove low molecular weight nonspecific proteins.

The purified recombinant 9-lipoxygenase having amino acid sequence as set forth in SEQ ID NO: 2 is run on a polyacrylamide and shows the band of purified protein having molecular weight near 100 kDa. (FIG. 2)

Figure 10A:
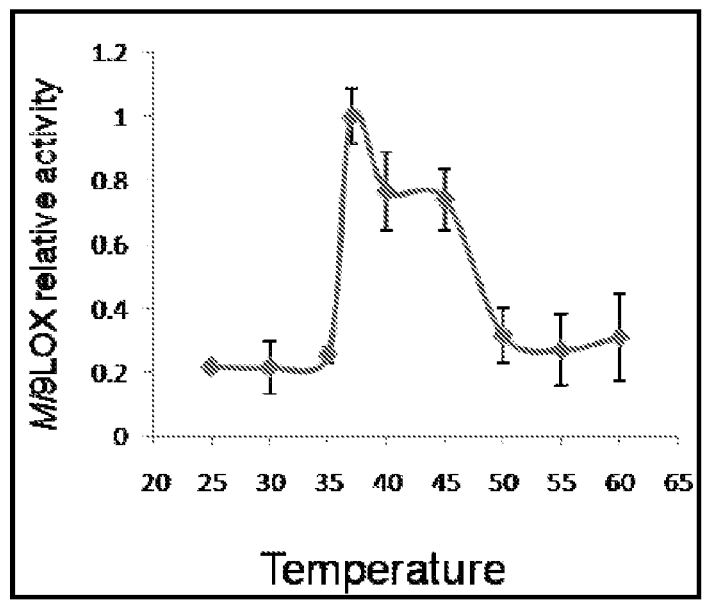
FIG. 10(a) depicts line graphs representing changes in the activity of Mi9LOX at different temperature.
Figure 10B:
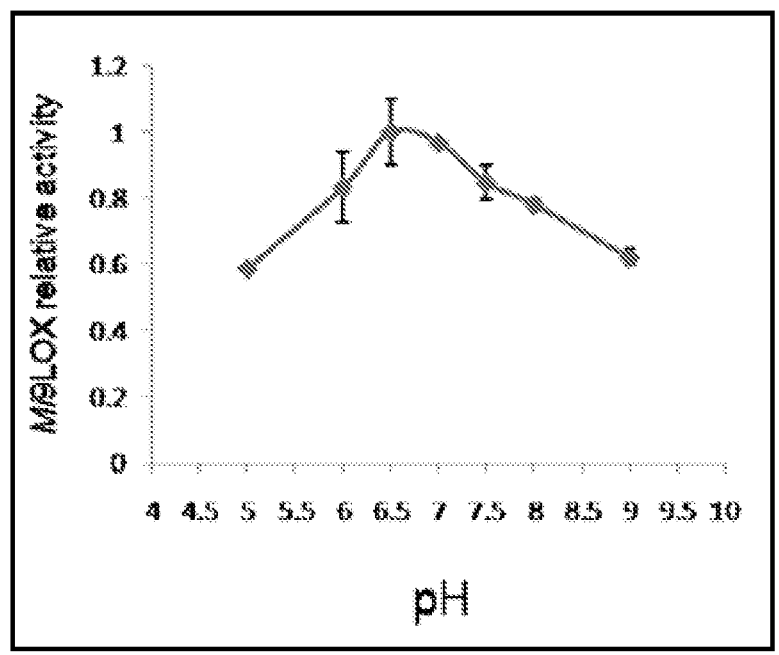
FIG. 10(b) depicts line graphs representing changes in the activity of Mi9LOX at different pH.

The recombinant 9-lipoxygenase synthesized by the process of the present invention is having optimal activity at temperatures ranging from about 30° C. to about 45° C. and a relative pH at 6 to 8. More preferably, the optimal temperature for activity of 9-lipoxygenase is 35° C. and optimal pH is 6.5 (FIG. 10(a) and FIG. 10(b)).

In another embodiment, the present invention provides a method for increasing the lactone content in fruits, the method comprises inserting the recombinant vector construct comprising polynucleotide having the nucleotide sequence as set forth in SEQ ID NO: 1 in a host cell from a fruit.

In another embodiment, the present invention provides in vivo transient over expression of 9-lipoxygenase in ripening mango fruits.

Figure 5:
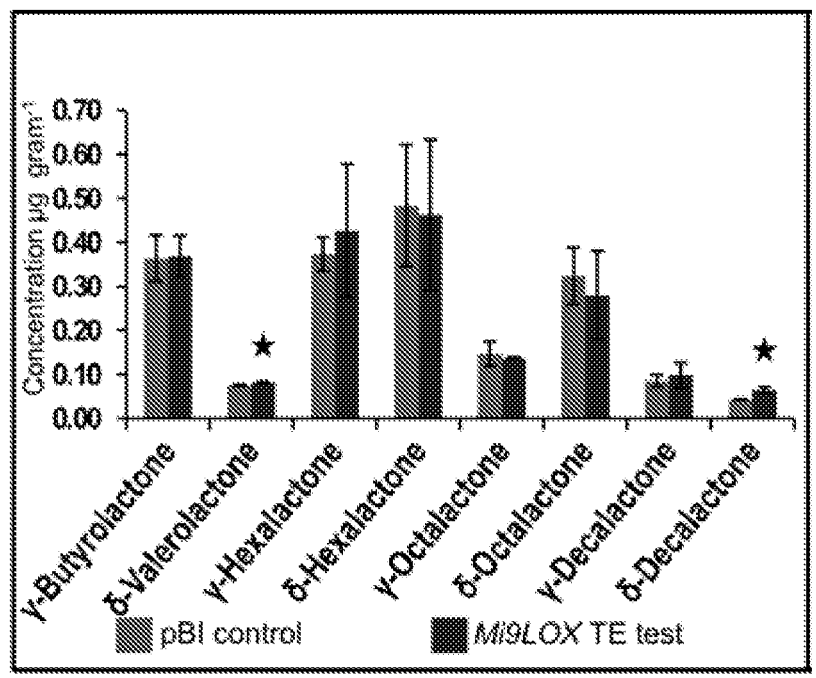
FIG. 5 depicts histograms representing changes in lactone content with respect to control upon transient over expression of Mi9LOX. Vertical bars represent standard error in the values of lactones from used data set, ★p≤0.1.

Accordingly, volatile compound analysis in mangoes post the agroinfiltration process of introducing plasmid vector comprising polynucleotide having the nucleotide sequence as set forth in SEQ ID NO: 1 transformed in the *Agrobacterium* GV3101 strain for transient expression studies indicated significant increase in δ-valerolactone and δ-decalactone. Over expression of polynucleotide having the nucleotide sequence as set forth in SEQ ID NO: 1 by transient expression resulted in the significant increase in the δ-valerolactone and δ-decalactone content which was 1.08 and 1.48 fold more, respectively compared to control tissue (FIG. 5).

Figure 6A:
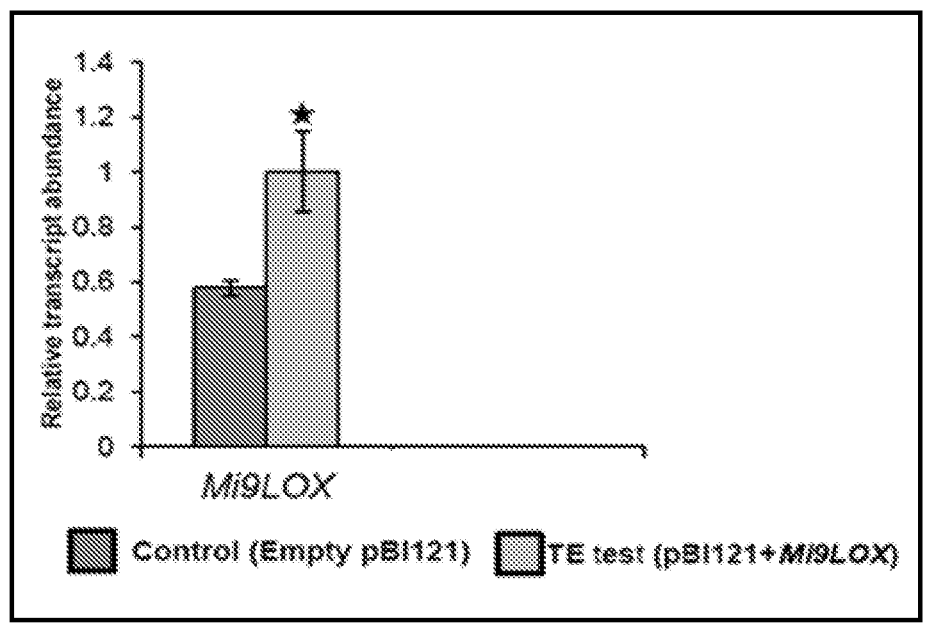
FIG. 6(*a*) depicts a histogram representing changes in the Mi9LOX transcripts level in the control and test tissues after agroinfiltration. Vertical bars represent standard error in the values of lactones from used data set, significance is represented as ★-p≤0.1.
Figure 6B:
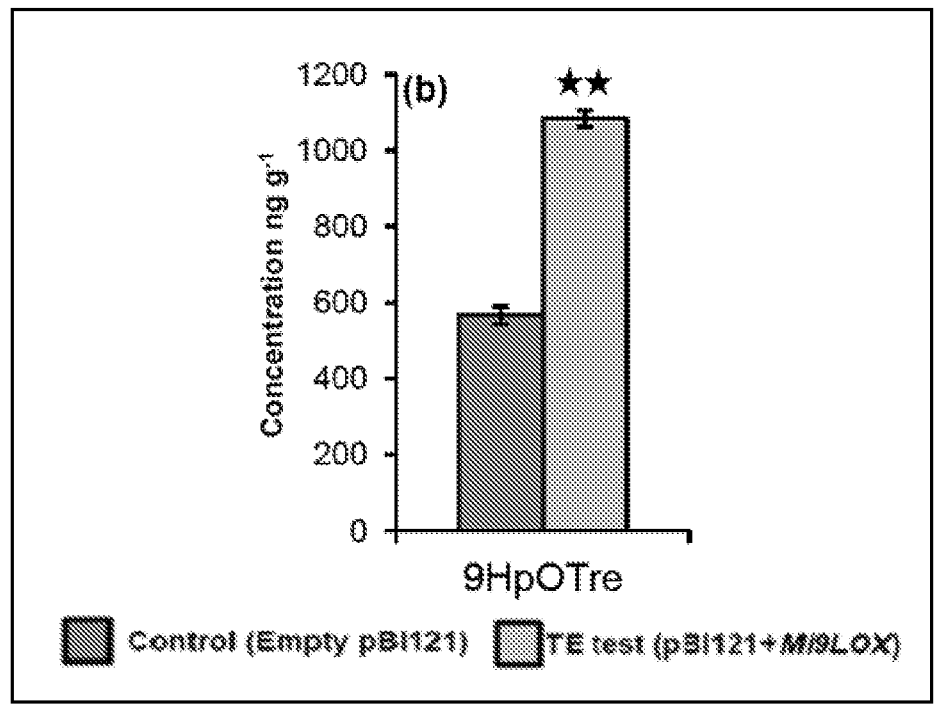

The transcript levels of Mi9LOX from the pulp tissue and skin tissue is exhibited in FIGS. 7(a, b, c) and 8(a, b, c) respectively. Mi9LOX transcripts from test tissues upon *Agrobacterium* infiltration showed significant increase of 1.73 as compared to the control tissues (FIG. 6a). Intermediate metabolite analysis of these tissues by HRMS revealed significant increase of 1.9 folds in the 9HpOTrE upon Mi9LOX over expression (FIG. 6b), whereas 9HpODE was not detected in the present analysis from control as well as test tissues.

Recombinant Mi9LOX utilized linoleic and linolenic acids as its substrate to depict its role in fatty acid metabolism. Significant increase in concentration of δ-valerolactone and δ-decalactone upon Mi9LOX over expression suggested involvement of MiLOX gene in lactone biosynthesis in mango.

The enzymatic activity of purified recombinant Mi9LOX using linoleic acid (LA) and linolenic acid (ALA) as substrates revealed formation of 9HpODE and 9HpOTrE products in FIG. 9(a, b, c, d, e, f).

EXAMPLES

Following examples are given by way of illustration therefore should not be construed to limit the scope of the invention.

Example 1: Source of Biological Material

The nucleotide sequence of interest was isolated from three mango varieties selected from the tissues of cv. Alphonso, cv. Pairi and cv. Kent. The cv. Alphonso and cv. Pairi varieties were collected from the Mango Research Sub Centre of Dr. Balasaheb Sawant Konkan Agricultural University, Dapoli situated at Deogad, Maharashtra, India, (16° 31' N, 73° 20' E). Fruits of cv. Kent were collected from the Regional Fruit Research Station, Dr. Balasaheb Sawant Konkan Agricultural University, Vengurle, Maharashtra, India (15° 51' N, 73° 39' E). Four developing and four ripening stages of all the three mango cultivars were collected. Developing stages were collected at 15 Days after Pollination (DAP), 30 DAP, 60 DAP and Mature raw stage (90DAP for cv. Alphonso and Pairi, 110DAP for cv. Kent). Fruits at these developing stages were harvested and pulp (mesocarp) and skin (exocarp) were separated immediately. The tissues were snap frozen in liquid nitrogen and stored at −80° C. till further use. A set of 12 fruits each for all the three cultivars were harvested at their respective mature raw stage and kept in the hay containing boxes at ambient temperature for ripening. Since three cultivars showed variation in the ripening duration, tissue for ripening stages were collected at Table Green, Mid Ripe, Ripe and Over Ripe stage (each stage is represented by days after harvest for cv. Alphonso as 5, 10, 15 and 20 days; for cv. Pairi as 4, 6, 8 and 10 days and for cv. Kent as 5, 8, 10 and 13 days, respectively) based on the skin colour, aroma and fruit softness. At each ripening stage fruits for each cultivar were removed from hay containing boxes, followed by separation of the mango pulp and skin, frozen in liquid nitrogen and stored at −80° C. till further use. For transient expression studies ethylene treated mangoes were collected as described by Chidley et al. (2013).

Example 2: RNA Isolation and cDNA Synthesis

Total RNA was isolated for all the tissues sampled for current study using RNeasy Plus mini kit (Quiagen, Venlo, Netherlands). Two microgram of total RNA was reverse transcribed for synthesis of cDNA using High Capacity cDNA reverse transcription kit (Applied Biosystem, Carlsbad, Calif., USA).

Example 3: Isolation of Open Reading Frames of 9-Lipoxygenase

The polynucleotide having nucleotide sequence as set forth in SEQ ID No.1 encoding 9-LOX was designed by designing gene specific primers from its available partial gene sequence having gene accession no. EU513272.1 retrieved from an earlier study by Pandit et al. (2010). For isolation of partial gene sequence of 9-LOX from Alphonso mango, degenerate primers viz. were designed by homology based approach aligning nucleotide sequences of EH2 from other plant species available in NCBI database. 5' and 3' RACE reactions were carried out using LF1 primer (SEQ ID NO: 4) and LR3 primer (SEQ ID NO: 5) to obtain cDNA ends of 9-LOX. The terminal primers, LOX_TF1 (SEQ ID NO: 6) and LOX_TR1 (SEQ ID NO: 7) were designed from obtained sequences to amplify a complete ORF of 9-lipoxygenase. Amplification using ripe mango cDNA; as template and the above mentioned terminal primers, sequencing for SEQ ID NO: 1 was carried out with the help of Advantage2 polymerase mix (Clonetech, USA) and cloned into pGEM-T easy vector, transformed into E. coli (Top 10) cells and presence of complete ORF of both the genes was confirmed by sequencing.

TABLE 1

Primers for designing polynucleotide having the nucleotide sequence as set forth in SEQ ID NO: 1 encoding 9-lipoxygenase

| Primer | Class | Primer Sequence | |
|---|---|---|---|
| Mi9LOX | | | |
| LF1 | B | GGGATCCGGACAATG GCAAACC | Seq Id No. 4 |
| LR3 | B | CCT CCA AGA ACT GGT CGT G | Seq Id No. 5 |
| LOX_TF1 | C | ATGGGGACAGTGGTG TTGATGAAG | Seq Id No. 6 |
| LOX_TR1 | C | CTAAATTGAAACACT GTTTGGAATTCC | Seq Id No. 7 |
| LOXpET101D F1 | D | CACCATGGGGACAGT GGTGTTGATGAAG | Seq Id No. 8 |
| LOXpET101D R1 | D | AATTGAAACACTGTT TGGAATTCCTTTG | Seq Id No. 9 |
| LOXpBI121F1 | E | AAAAAAGGATCCATG GGGACAGTGGTGTTG ATGAAG | Seq Id No. 10 |

TABLE 1-continued

Primers for designing polynucleotide having the nucleotide sequence as set forth in SEQ ID NO: 1 encoding 9-lipoxygenase

| Primer | Class | Primer Sequence | |
|---|---|---|---|
| LOXpBI121R1 | E | AAA AAA GGA TCC CTA AAT TGA AAC ACT GTT TGG AAT TCC | Seq Id No. 11 |

The obtained sequences upon in silico analysis showed presence of complete ORF of SEQ ID NO:1 having 2526 bp, along with only 3' UTR (167 bp) was observed (Table 2). The complete ORF of isolated LOX showed nucleotide sequence similarity with other plant linoleate 9-lipoxygenase. The isolated *Mangifera indica* 9-lipoxygenase (Mi9LOX) from Alphonso mango encodes protein having sequence as set forth in SEQ ID NO: 2 with length of 841 aa and shows maximum similarity with 9LOX from *Litchi chinensis* (78%).

TABLE 2

Nucleotide and polypeptide sequence identity of lipoxygenase

| | Mi9LOX |
|---|---|
| ORF length (nucleotides) | 2526 |
| 3' UTR length (nucleotides) | 167 |
| 5' UTR length (nucleotides) | — |
| Nucleotide sequence similarity | *Citrus sinensis* 9LOX (80%) *Populus euphratica* 9LOX (78%) *Prunus mume* 9LOX (77%) |
| In-silico translated protein | Mi9LOX |
| Protein length (amino acids) | 841 |
| Calculated molecular weight (kDa) | 96.3 |

RACE primers were designed from partial lipoxygenase gene sequence from Alphonso NCBI Accession no-EU513272.1 (Pandit et al., 2010). RACE primers designed have the following nucleotide sequences are represented below:

Seq Id No. 4 Forward Primer (LF1):
GGGATCCGGACAATGGCAAACC

Seq Id No. 5 Reverse Primer (LR3)-
CCTCCAAGAACTGGTCGTG

5' and 3' RACE bands eluted, cloned in pGEM-T Easy vector, transformed in E. coli Top10 competent cells and cloned plasmids sequenced.

Terminal primers for full length gene isolation were as follows:

Seq Id No. 6: Forward Primer: LOX_TF1-
ATGGGGACAGTGGTGTTGATGAAG

Seq Id No. 7: Reverse Primer: LOX_TR1-
CTAAATTGAAACACTGTTTGGAATTCC

An approximately ~2.5 kb size band was eluted (FIG. 3), cloned in pGEM-T Easy vector, transformed in E. coli Top10 competent cells and the cloned plasmids were sequenced.

Example 4: Cultivation of E. coli Cells Transformed with Polynucleotide Having Sequence as Set Forth in SEQ ID NO: 1 Encoding 9-Lipoxygenase A 2526 bp full length polynucleotide having sequence as set forth in SEQ ID No: 1 encoding 9-lipoxygenase sequence was amplified and cloned into plasmid pET101D/TOPO (Invitrogen) using primers having SEQ ID NO: 8 and SEQ ID No: 9. The plasmid vector comprising the polynucleotide sequence was transformed in E. coli (Rosetta) cells. A starter inoculum comprising a single colony in 20 ml TB media was incubated for 12 hrs at 37° C. Post incubation, 1% of the inoculum was inoculated in 1000 ml of the TB media and further incubated at 37° C. The absorbance of the inoculum was determined till a value of 0.5 or 0.6 was obtained indicating the growth of the culture. After achieving the desired optical density, the culture was induced with 0.2 mM IPTG. The expression culture was incubated for 16 to 20 hours at 18° C. After incubation, the cells were subjected to cell lysis and harvested by sonication to obtain the 9-lipoxygenase protein.

Example 5: Purification of Recombinant 9-Lipoxygenase

The poly-histidine tag was inserted onto the target gene by site-directed mutagenesis or by a polymerase chain reaction optimally such that the six histidine residues were expressed at the C or N terminus of the expressed protein. Accordingly, the DNA fragments coding for the poly-histidine affinity tag were synthesized from synthetic oligonucleotides and cloned into an appropriate location in the plasmid pET101D/TOPO. The expressed recombinant polypeptide 9-lipoxygenase protein having the histidine residue tag at the N-terminus was purified by Ni-NTA affinity matrix. Nickel loaded NTA agarose beads were used as a resin in the separation column and the sample comprising the expressed lipoxygenase was allowed to pass the column. After which, an equilibration buffer having pH 7 was poured in controlled quantities to increase the binding of the protein to the NTA beads. The column was washed with 50 mM imidazole in sodium phosphate buffer pH-7.0 to remove contaminants. Bound recombinant 9 lipoxygenase protein was eluted in 250 mM imidazole in sodium phosphate buffer pH-7.0. Further eluted fractions were passed through 50 kDa cutoff column to remove low molecular weight contaminants from eluted fractions.

Example 6: In Vivo Transient Over Expression of 9-Lipoxygenase

Figure 4A:
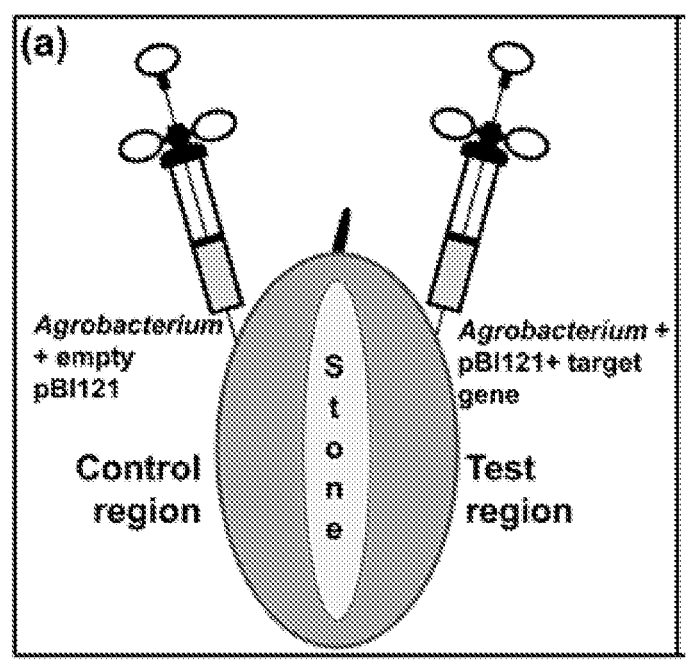
FIG. 4(*a*) represents drawings related to the agroinfiltration of the target gene in mangoes; the process of agroinfiltration of empty pBI121 (Control) and pBI121+ target gene (test) constructs in two different regions of the same mango fruit separated by fruit stone, FIG. 4(*b*) represents images of Alphonso mango fruit after subjection to agroinfiltration and Gus staining.

The full length polynucleotide sequence (SEQ ID NO: 1) encoding 9-lipoxygenase (SEQ ID NO: 2) was cloned into the pBI121 plant expression vector between CaMV 35S promoter and GusA gene. Terminal primers were designed (SEQ ID NO: 10 and SEQ ID NO: 11) to clone genes at BamHI restriction site. The resulted correct oriented construct pBI121+Mi9LOX and pBI121 empty vector were transformed in the Agrobacterium GV3101 strain for transient expression studies. Separate Agrobacterium cultures (5 mL) were initiated from individual colonies in YEB medium having appropriate antibiotics and incubated overnight at 28° C. This culture was transferred to 50 mL induction medium (0.5% beef extract, 0.1% yeast extract, 0.5% peptone, 0.5% sucrose, 2 mM MgSO4, 20 mM acetosyringone, 10 mM MES, pH 5.6) having appropriate antibiotics, and again grown overnight. On the succeeding day, cultures were recovered by centrifugation, resuspended in infiltration medium (10 mM $MgCl_2$, 10 mM MES, 200 mM acetosyringone, pH 5.6) till optical density reaches 1.0. This suspension was again incubated at 28° C. with gentle agitation for 2 hrs. Over expression studies for 9LOX was carried out by Agrobacterium mediated infiltration in ethylene treated mango fruits at 3DAH stage by using hypodermic syringe (FIG. 4a). Equal volumes of pBI121+Mi9LOX and pBI121 construct containing cultures were used for infiltration in two different halves of same mango fruit separated by fruit stone. Set of five distinct mango fruits were used for the overexpression study as data set. Infiltrated fruits were kept at 25° C. for 2 days in 12 hr dark and 12 hr light conditions, after 2 days; part from each fruit halves was checked by the Gus staining (Kapila et al. 1997; Spolaore et al. 2001) to confirm expression of Mi9LOX under 35S promoter along with GusA, remaining part of fruit pulp stored in −80° C. until used for the lactone analysis by gas chromatography.

Figure 4B:
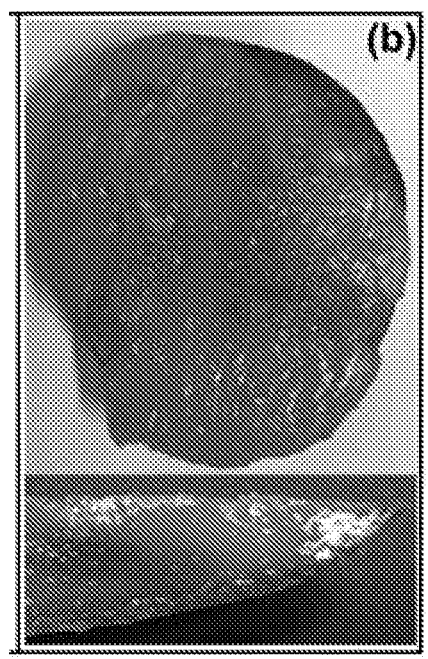

Ethylene treated fruits were selected for this experiment in view of a previous study by the inventors of the present application revealing early appearance of lactones and accelerated ripening of Alphonso fruits upon exogenous ethylene treatment without any quantitative variation in the lactone content (Chidley et al. 2013). Thus, ethylene treated mangoes were ideal for Agrobacterium infiltration studies as Agrobacterium infiltrated fruits cannot be incubated for more than 2 days due to the risk of bacterial and fungal infection owing to fruit injury during infiltration. Two days post infiltration, a part of fruit was checked by Gus staining (FIG. 4b) to confirm expression of GusA along with the Mi9LOX gene. The remaining tissue was used for the lactone content analysis. The lactones were analysed from control and test region of fruits from Mi9LOX sets. Total 8 lactones viz. γ-butyrolactone, δ-valerolactone, γ-hexalactone, δ-hexalactone, γ-octalactone, δ-octalactone, γ-decalactone and δ-decalactone were detected from all the tissues in GC-MS analysis. Quantitative analysis of lactones by GC-FID showed increased content of few lactones in both sets (FIG. 5). Over expression of recombinant 9-lipoxygenase (SEQ ID NO:2) by transient expression resulted in the significant increase in δ-valerolactone and δ-decalactone content which was 1.08 and 1.48 fold more, respectively compared to control tissue.

Example 7: Enzyme Assays of Recombinant Mi9LOX

The recombinant 9-lipoxygenase (Mi9LOX) activity assays was initially carried out in 250 μl final volume of 100 mM phosphate citrate buffer pH 7.0 at 30° C. containing 200 μM substrate (LA/ALA) and 0.005% Tween20. The activity was measured by formation of the conjugated diene at absorbance of 234 nm, applying an extinction coefficient 25000 $M^{-1}$ $cm^{-1}$ for both the substrates. $A_{234}$ at $0^{th}$ min for each reaction is considered as blank and subtracted from $A_{234}$ for given time (t). Similar activity assays were also performed with protein expressed from empty vector for the confirmation of Mi9LOX activity. Optimum pH was determined by calculating activity at varied range of pH in phosphate citrate buffer at 30° C., whereas temperature optima was determined by calculating recombinant 9-lipoxygenase activity in phosphate citrate buffer pH 7 at various temperatures.

After spectrophotometric measurement of catalytic activity of the in-silico translated protein, products were extracted in a solvent system comprising chloroform:methanol (2:1);

completely dried in vacuum evaporator and reconstituted in the methanol. These assay extracts were then used for UPLC coupled Q Exactive orbitrap HRMS (Thermo scientific, MA, USA) analysis for the product confirmation. Extracted compounds from the assay reactions were separated by water (A): methanol (B) solvent gradient, at 0 min 70% (A)/30% (B); 0-2 min 50% (A)/50% (B); 2-12 min 0% (A)/100% (B), hold for 2 min and again back to 70% (A)/30% (B) in 3 min with 2 min hold at flow rate 500 µl min$^{-1}$.

The purified recombinant 9-lipoxygenase having amino acid sequence as set forth in SEQ ID NO: 2 used linoleic acid (LA) and alpha linolenic acid (ALA) as substrates. Activity of the recombinant 9-lipoxygenase protein was measured spectrophotometrically at 234 nm by the formation of conjugated dienes. For unit calculations, molar extinction coefficient for hydroperoxy linoleate and linolenate was considered 25000 cm$^{-1}$M$^{-1}$. 9HpODE and 9HpOTrE products formed by the activity of Mi9LOX on LA and ALA respectively were confirmed by UPLC-HRMS. Identification of 9HpODE and 9HpOTrE was done by monitoring [M+Na]$^+$ 335.4 and [M+Na]$^+$ 333.4 molecular ions, respectively as well as matching retention time with that of authentic standards. Biochemical characterization of Mi9LOX revealed activity at wide range of pH (6-8) with optima at pH 6.5, whereas 40% reduction in the activity was evinced at pH 5 and 9(FIG. 10(b)). Most of the lipoxygenases are known to have acidic pH optima and similar finding was observed for the mango Mi9LOX (Padilla et al. 2012; Huang and Schwab 2011; Santino et al. 2005). Activity profiles of Mi9LOX at varied temperatures showed stable activity of enzyme at 37° C. to 45° C., with temperature optima at 37.0° C. (FIG. 10(a)). 75% reduction in the activity was observed at 35° C. and 69% reduced activity was seen at 50° C. The enzyme kinetics was carried out with LA and ALA and the calculated Km values (Table 3) from in vitro studies revealed that Mi9LOX has more affinity towards ALA than LA. This suggests adaption of enzyme for in vivo conditions of substrate availability, as increased ALA and decreased LA content was observed during ripening of mango fruits in an earlier study by the inventors of the present application.

TABLE 3

Activity profiles of Mi9LOX

|  | Mi9LOX |
|---|---|
| Optimum temperature | 37° C. |
| Optimum pH | 6.5 |
| Vmax (µM min$^{-1}$mg$^{-1}$) | LA- 611.11 ± 55.55 |
|  | ALA- 279.84 ± 5.87 |
| Km (mM) | LA- 0.3535 ± 0.028 |
|  | ALA- 0.0614 ± 8E$^{-5}$ |
| Vmax/Km min$^{-1}$mg$^{-1}$) | LA- 1.728 |
|  | ALA- 4.557 |

Example 8: Transcript Abundance of Mi9LOX

Figure 7A:
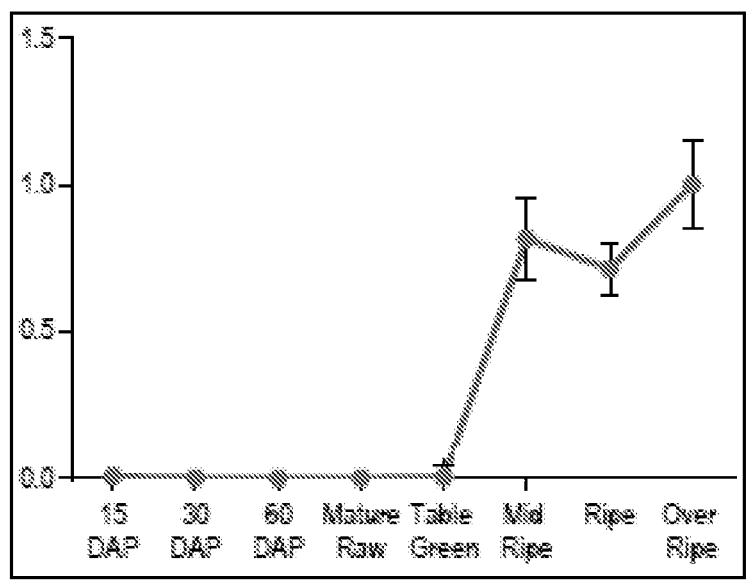
FIG. 7(*a*) depicts transcript profiles of Mi9LOX from pulp tissue of various fruit development and ripening stages of Alphonso mango cultivars. Vertical bars at each data point represent standard error in the relative quantification among the biological replicates. X axis represents fruit development and ripening stages and Y axis represents relative transcript abundance.
Figure 7B:
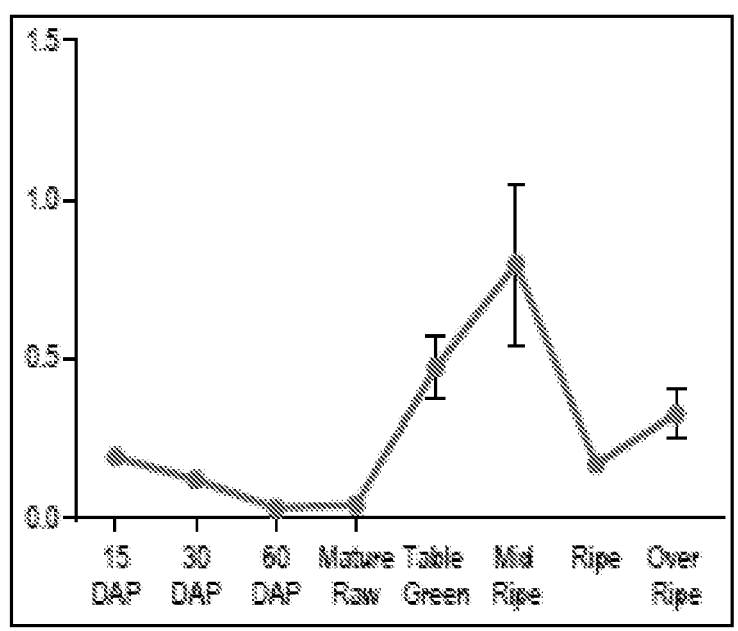
Figure 7C:
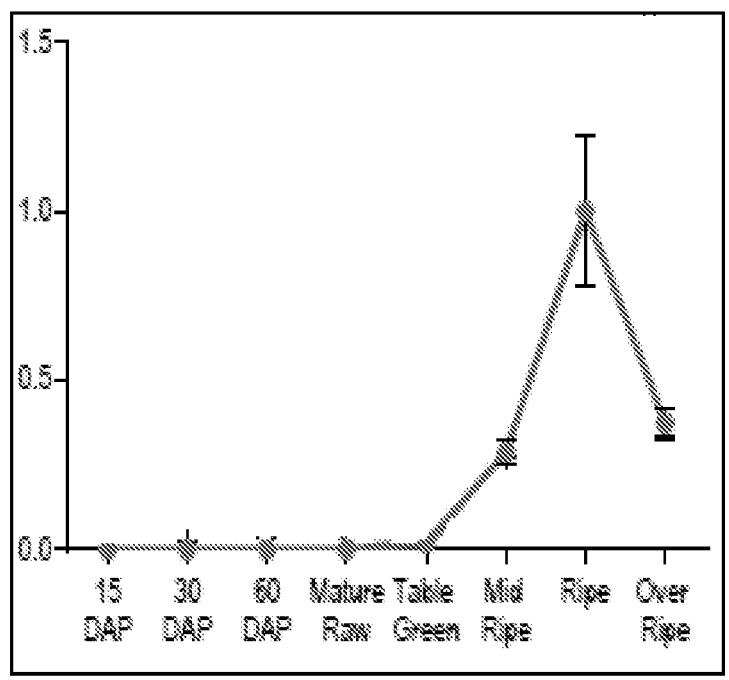
Figure 8A:
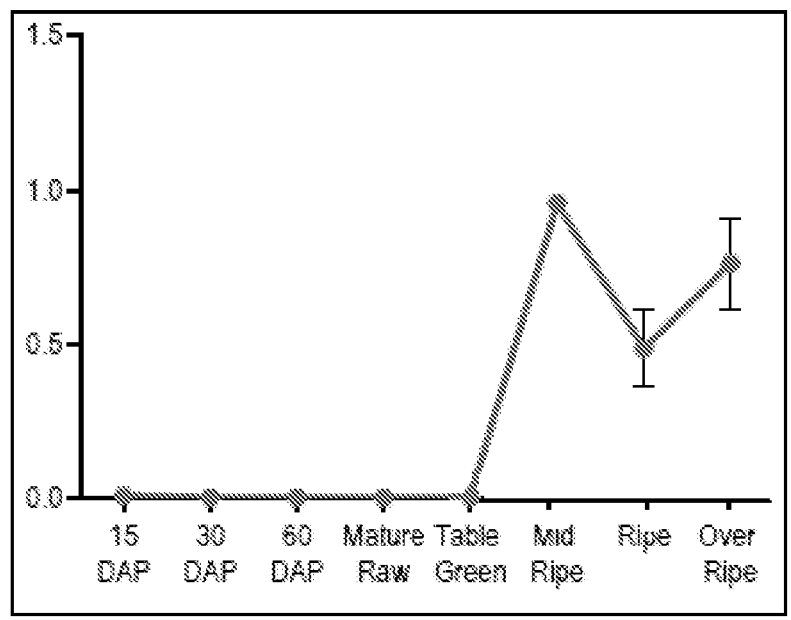
FIG. 8(*a*) depicts the transcript profiles of Mi9LOX from skin tissue of various fruit development and ripening stages of Alphonso mango cultivars. Vertical bars at each data point represent standard error in the relative quantification among the biological replicates. X axis represents fruit development and ripening stages and Y axis represents relative transcript abundance.
Figure 8B:
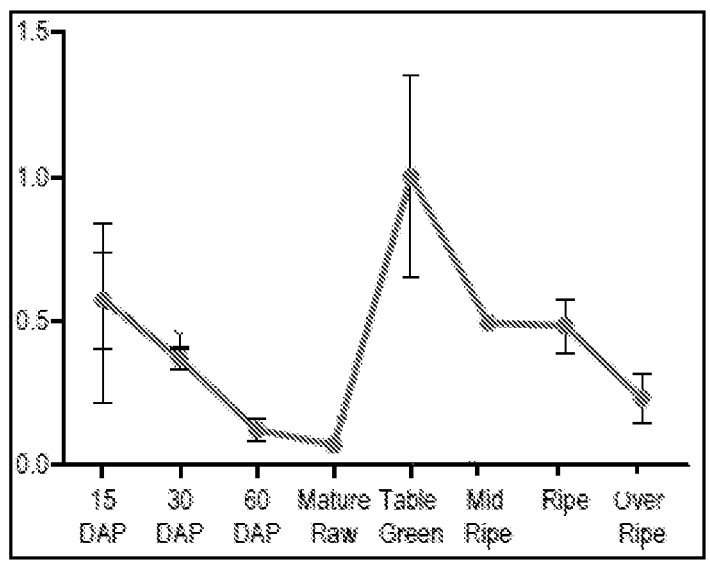
Figure 8C:
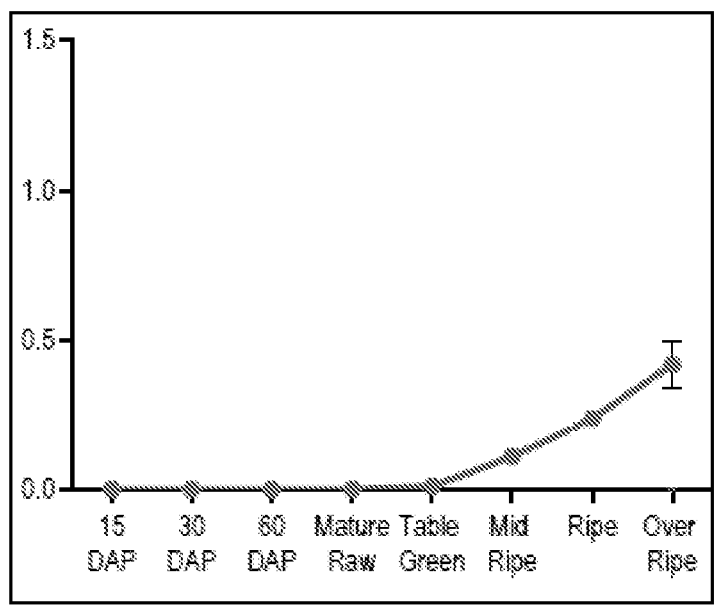
Figure 9A:
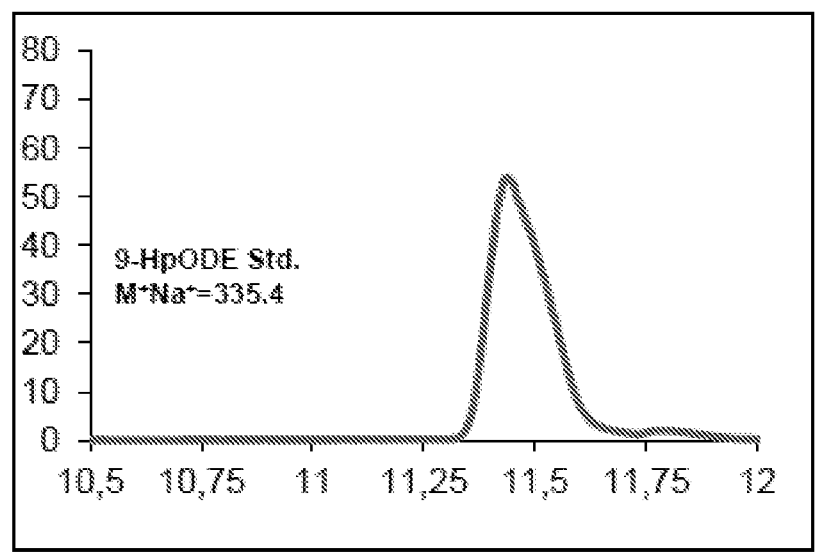
FIG. 9(*a*) depicts the extracted ion chromatograms from High Resolution Mass Spectrometry (HRMS) analysis for product identification of Mi9LOX assay reactions, HpODE standard. X-axis represents retention time (min) and Y-axis represents relative intensity.
FIG. 9(e) depicts the extracted ion chromatograms from High Resolution Mass Spectrometry (HRMS) analysis for products formed in assay reactions of Mi9LOX with substrate linolenic acid. X-axis represents retention time (min) and Y-axis represents relative intensity.
FIG. 9(f) depicts the extracted ion chromatograms from High Resolution Mass Spectrometry (HRMS) analysis for product identification of Mi9LOX assay reactions, for the protein expressed from empty vector with substrates linolenic acid. X-axis represents retention time (min) and Y-axis represents relative intensity.
Figure 9B:
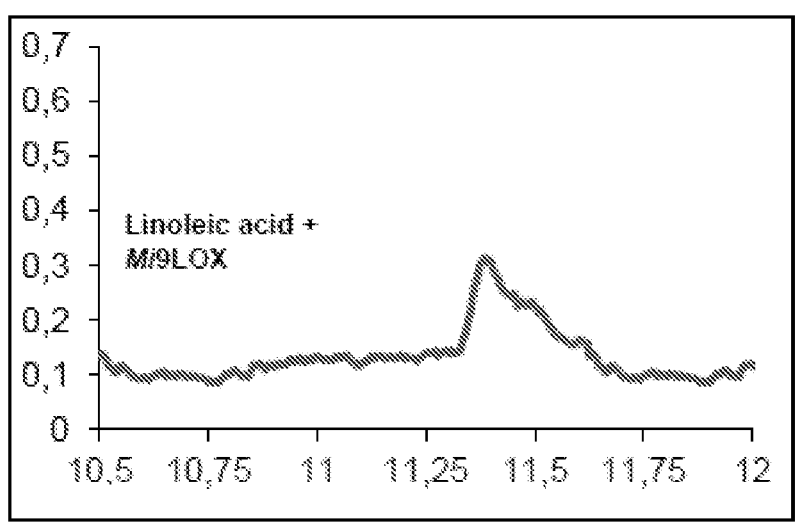
Figure 9C:
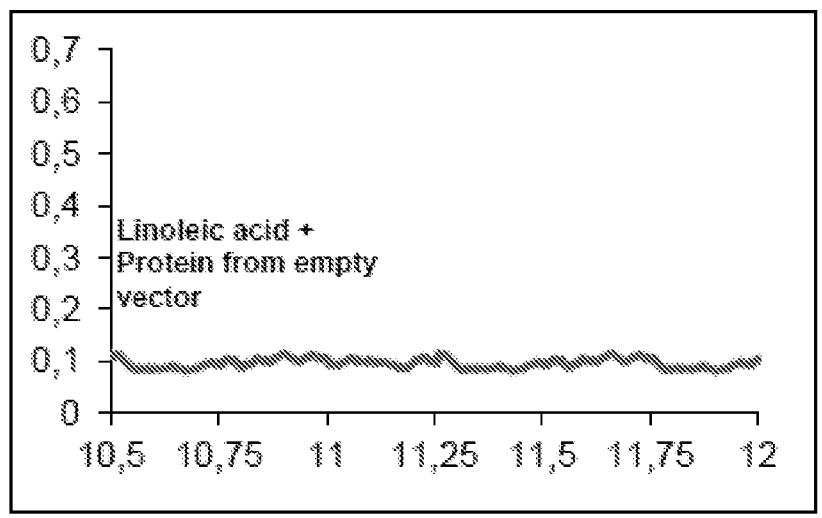
Figure 9D:
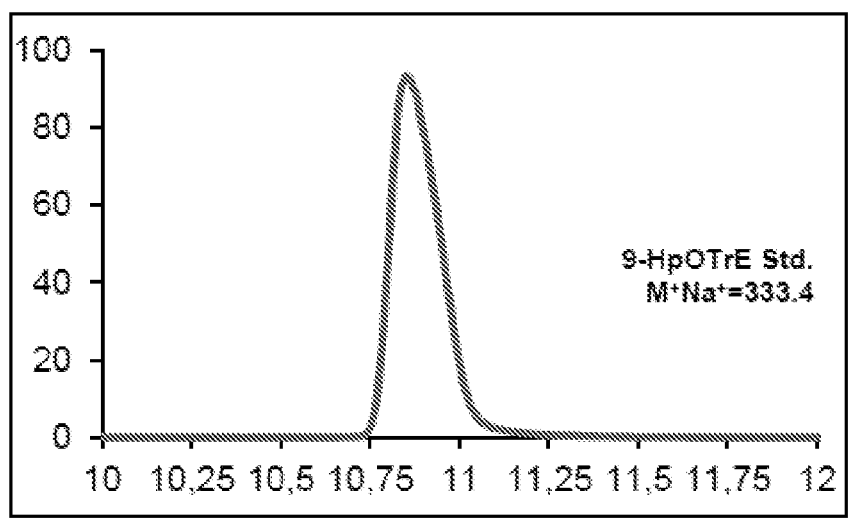
Figure 9E:
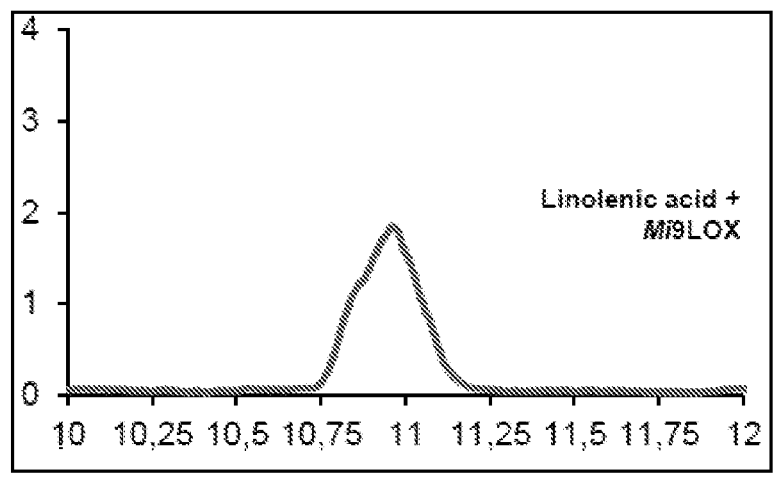
Figure 9F:
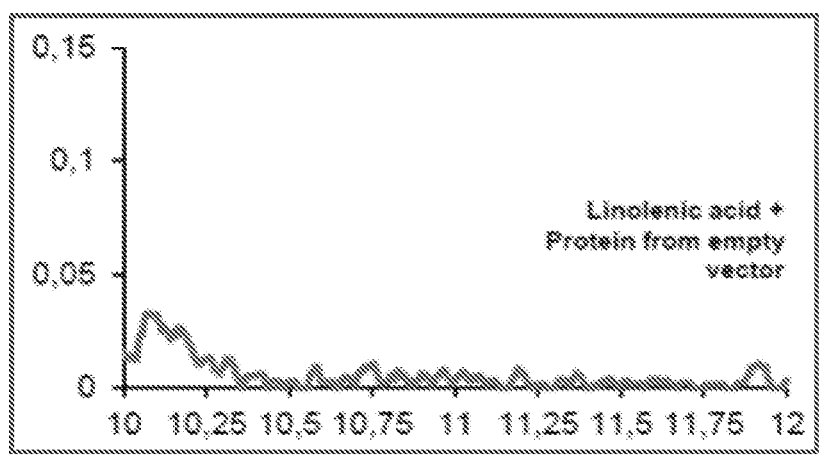

The transcript abundance of Mi9LOX gene was studied in pulp and skin tissues of fruit of Alphonso, Pairi and Kent cultivars at various stages of fruit development and ripening. Transcript levels of Mi9LOX gene from three cultivars at their maxima were not significantly different; however their differential expression was evinced at various ripening stages and in pulp and skin tissues of the three cultivars. Transcript level of each gene at its maximum expression was considered as 1 and its relative expression in pulp and skin of various stages was represented across cultivars. FIG. 7(a) depicts the transcript profile of Mi9LOX from pulp tissue of various fruit development and ripening stages of Alphonso cultivar. FIG. 7(b) depicts the transcript profile of Mi9LOX from pulp tissue of various fruit development and ripening stages of Pairi cultivar. FIG. 7(c) depicts the transcript profile of Mi9LOX from pulp tissue of various fruit development and ripening stages of Kent cultivar. FIG. 8(a) depicts the transcript profile of Mi9LOX from skin tissue of various fruit development and ripening stages of Alphonso cultivar. FIG. 8(b) depicts the transcript profile of Mi9LOX from skin tissue of various fruit development and ripening stages of Pairi cultivar. FIG. 8(c) depicts the transcript profile of Mi9LOX from skin tissue of various fruit development and ripening stages of Kent cultivar. All the three cultivars showed ripening specific appearance of Mi9LOX transcripts. Relative transcript profiles of Mi9LOX Alphonso pulp revealed their high abundance through mid-ripe stage to over ripe stage, whereas, slight reduction in their level was observed at post mid ripe stage in case of the skin tissue. Mi9LOX transcripts from Pairi pulp and skin tissues showed their maximum level at table green stage except for optimum level for Mi9LOX at mid ripe stage of Pairi pulp. Reduction in the Mi9LOX level was evinced in further ripening stages of Pairi tissues. In the case of Kent pulp, Mi9LOX transcript abundance was the highest at ripe stage, whereas in case of Kent skin tissue transcript level was higher at over ripe stage.

ADVANTAGE OF THE PRESENT INVENTION

The present invention provides methods for production of 9-lipoxygenase enzyme in enhanced quantities by expressing the polynucleotide having nucleotide sequence as set forth in SEQ ID NO: 1 in appropriate expression vector systems and the subsequent production of lactones in other mango cultivars.

We claim:

1. A polynucleotide having the nucleotide sequence as set forth in SEQ ID NO: 1 encoding a recombinant protein 9-lipoxygenase.

2. The polynucleotide of claim 1, wherein the recombinant protein 9-lipoxygenase has the amino acid sequence as set forth in SEQ ID NO: 2.

3. The polynucleotide of claim 1, wherein said polynucleotide is a cDNA.

4. A plasmid expression vector comprising the polynucleotide of claim 1, wherein the plasmid expression vector is selected from the group consisting of a plant plasmid expression vector and a bacterial plasmid expression vector.

5. The plasmid expression vector of claim 4, wherein the plasmid expression vector is selected from the group consisting of pBI121, pET101D, and pGEMT.

6. A host cell comprising the plasmid expression vector of claim 5, wherein the host cell is selected from the group consisting of *E. coli* BL21, *E. coli* Rosetta, and *Agrobacterium* (GV3101).

7. A process for synthesis of recombinant 9 lipoxygenase, the process comprising:
   (a) synthesizing polynucleotide having the nucleotide sequence as set forth in SEQ ID NO: 1 with primers having a sequence selected from the group consisting of SEQ ID NO: 4, SEQ ID NO: 5, SEQ ID NO: 6, and SEQ ID NO: 7;
   (b) cloning the polynucleotide having the nucleotide sequence as set forth in SEQ ID NO: 1 obtained in (a) into a plasmid expression vector using expression vector specific primers to obtain a recombinant plasmid expression vector;
   (c) transforming the recombinant plasmid expression vector obtained in (b) into a host cell to obtain a transformed host cell;
   (d) culturing the transformed host cell obtained in (c) at a temperature from 12° C. to 25° C. in a culture medium;
   (e) separating the recombinant host cells from the culture medium; and
   (f) performing lysis and sonication of recombinant host cells to isolate the recombinant 9 lipoxygenase.

8. The process of claim 7, wherein the plasmid expression vector is selected from the group consisting of a plant expression vector pBI121 and a bacterial expression vector pET101D.

9. The process of claim 7, wherein the expression vector specific primers are selected from the group consisting of SEQ ID NO: 8, SEQ ID NO: 9, SEQ ID NO: 10, and SEQ ID NO: 11.

10. The process of claim 7, wherein the host cell is selected from the group consisting of *E. coli* BL21, *E. coli* Rosetta, and *Agrobacterium* (GV3101).

11. The plasmid expression vector of claim 5, wherein the plasmid expression vector is pET101D.

12. The host cell of claim 6, wherein the host cell is *E. coli* Rosetta.

* * * * *